(12) United States Patent
Nguyen

(10) Patent No.: US 9,409,872 B1
(45) Date of Patent: Aug. 9, 2016

(54) FUMARATE COMPOUNDS, PHARMACEUTICAL COMPOSITIONS THEREOF, AND METHODS OF USE

(71) Applicant: Mark Quang Nguyen, San Jose, CA (US)

(72) Inventor: Mark Quang Nguyen, San Jose, CA (US)

(73) Assignee: Mark Quang Nguyen, San Jose, CA (US)

( * ) Notice: Subject to any disclaimer, the term of this patent is extended or adjusted under 35 U.S.C. 154(b) by 0 days.

(21) Appl. No.: 14/623,188

(22) Filed: Feb. 16, 2015

(51) Int. Cl.
| | |
|---|---|
| *A61K 31/513* | (2006.01) |
| *C07D 239/54* | (2006.01) |
| *A61K 9/00* | (2006.01) |
| *A61K 45/06* | (2006.01) |

(52) U.S. Cl.
CPC ............ *C07D 239/54* (2013.01); *A61K 9/0053* (2013.01); *A61K 31/513* (2013.01); *A61K 45/06* (2013.01)

(58) Field of Classification Search
CPC .................................................. C07D 239/54
See application file for complete search history.

(56) References Cited

U.S. PATENT DOCUMENTS 8,637,529 B2 * 1/2014 Woller ................. C07D 487/04
514/262.1

FOREIGN PATENT DOCUMENTS

DE 2012644 A1 * 9/1971 ........... C07D 213/30
JP 10001521 A * 1/1998

OTHER PUBLICATIONS

Goodman & Gilman's, Manual of Pharmacology and Therapeutics 336-348 (L.L. Bruton et al., eds., 2008).*
O.E. Lutz, 110(1) Journal of the Chemical Society, Abstracts, 73-74 (1916).*
CAS Abstract JP 10001521 A, Accession No. 1998:25419 (1998).*
T. Imagawa et al., 7 Chemistry Letters, 903-904 (1981).*
T. Kato et al., 25 Chemical & Pharmaceutical Bulletin, 491-494 (1977).*
CAS Abstract of 13 Gaodeng Xuexiao Huaxue Xuebao, 1561-1563 (1992), Accession No. 1993:517198 (1993).*
CAS Reg No. 556022-68-5 (Entered STN: Jul. 28, 2003).*
CAS Reg No. 556023-70-2 (Entered STN: Jul. 28, 2003).*
CAS Reg No. 871807-04-4 (Entered STN: Jan. 12, 2006).*

* cited by examiner

*Primary Examiner* — Alexander R Pagano

(57) ABSTRACT

Fumarate compounds, pharmaceutical compositions comprising the fumarate compounds, and methods of using fumarate compounds and pharmaceutical compositions for treating neurodegenerative, inflammatory, and autoimmune disorders including multiple sclerosis, psoriasis, irritable bowel disorder, ulcerative colitis, arthritis, chronic obstructive pulmonary disease, asthma, Parkinson's disease, Huntington's disease, and amyotrophic lateral sclerosis are disclosed.

13 Claims, No Drawings

FUMARATE COMPOUNDS, PHARMACEUTICAL COMPOSITIONS THEREOF, AND METHODS OF USE

FIELD

Disclosed herein are fumarate compounds, pharmaceutical compositions comprising fumarate compounds, and methods of using fumarates and pharmaceutical compositions thereof for treating neurodegenerative, inflammatory, and autoimmune diseases including multiple sclerosis, psoriasis, irritable bowel disorder, ulcerative colitis, arthritis, chronic obstructive pulmonary disease, asthma, Parkinson's disease, Huntington's disease, and amyotrophic lateral sclerosis.

BACKGROUND

Fumaric acid esters (FAEs) are approved in United States for the treatment of multiple sclerosis, are being evaluated in the United States for the treatment of psoriasis, and have been proposed for use in treating a wide range of immunological, autoimmune, and inflammatory diseases and conditions.

FAEs and other fumaric acid derivatives have been proposed for use in treating a wide-variety of diseases and conditions involving immunological, autoimmune, and/or inflammatory processes including psoriasis (Joshi and Strebel, WO 1999/49858; U.S. Pat. No. 6,277,882; Mrowietz and Asadullah, Trends Mol Med 2005, 111(1), 43-48; and Yazdi and Mrowietz, Clinics Dermatology 2008, 26, 522-526); asthma and chronic obstructive pulmonary diseases (Joshi et al., WO 2005/023241 and US 2007/0027076); cardiac insufficiency including left ventricular insufficiency, myocardial infarction and angina pectoris (Joshi et al., WO 2005/023241; Joshi et al., US 2007/0027076); mitochondrial and neurodegenerative diseases such as Parkinson's disease, Alzheimer's disease, Huntington's disease, retinopathia pigmentosa and mitochondrial encephalomyopathy (Joshi and Strebel, WO 2002/055063, US 2006/0205659, U.S. Pat. No. 6,509,376, U.S. Pat. No. 6,858,750, and U.S. Pat. No. 7,157,423); transplantation (Joshi and Strebel, WO 2002/055063, US 2006/0205659, U.S. Pat. No. 6,359,003, U.S. Pat. No. 6,509,376, and U.S. Pat. No. 7,157,423; and Lehmann et al., Arch Dermatol Res 2002, 294, 399-404); autoimmune diseases (Joshi and Strebel, WO 2002/055063, U.S. Pat. No. 6,509,376, U.S. Pat. No. 7,157,423, and US 2006/0205659) including multiple sclerosis (MS) (Joshi and Strebel, WO 1998/52549 and U.S. Pat. No. 6,436,992; Went and Lieberburg, US 2008/0089896; Schimrigk et al., Eur J Neurology 2006, 13, 604-610; and Schilling et al., Clin Experimental Immunology 2006, 145, 101-107); ischemia and reperfusion injury (Joshi et al., US 2007/0027076); AGE-induced genome damage (Heidland, WO 2005/027899); inflammatory bowel diseases such as Crohn's disease and ulcerative colitis; arthritis; and others (Nilsson et al., WO 2006/037342 and Nilsson and Muller, WO 2007/042034).

The mechanism of action of fumaric acid esters is believed to be mediated by pathways associated with the immunological response. For example, FAEs invoke a shift from a Th1 to Th2 immune response, favorably altering the cytokine profile; inhibit cytokine-induced expression of adhesion molecules such as VCAM-1, ICAM-1 and E-selectin, thereby reducing immune cell extravasation; and deplete lymphocytes through apoptotic mechanisms (Lehmann et al., J Investigative Dermatology 2007, 127, 835-845; Gesser et al., J Investigative Dermatology 2007, 127, 2129-2137; Vandermeeren et al., Biochm Biophys Res Commun 1997, 234, 19-23; and Treumer et al., J Invest Dermatol 2003, 121, 1383-1388).

Recent studies suggest that FAEs are inhibitors of NF-κB activation, a transcription factor that regulates the inducible expression of proinflammatory mediators (D'Acquisto et al., Molecular Interventions 2002, 2(1), 22-35). Accordingly, FAEs have been proposed for use in treating NF-κB mediated diseases (Joshi et al., WO 2002/055066; and Joshi and Strebel, WO 2002/055063, US 2006/0205659, U.S. Pat. No. 7,157,423 and U.S. Pat. No. 6,509,376). Inhibitors of NF-κB activation have also been shown to be useful in angiostatic therapy (Tabruyn and Griffioen, Angiogenesis 2008, 11, 101-106), inflammatory bowel disease (Atreya et al., J Intern Med 2008, 263(6), $59_{1-6}$); and in animal models of diseases involving inflammation including neutrophilic alveolitis, asthma, hepatitis, inflammatory bowel disease, neurodegeneration, ischemia/reperfusion, septic shock, glomerulonephritis, and rheumatoid arthritis (D'Acquisto et al., Molecular Interventions 2002, 2(1), 22-35).

Studies also suggest that NF-κB inhibition by FAEs may be mediated by interaction with tumor necrosis factor (TNF) signaling. Dimethyl fumarate inhibits TNF-induced tissue factor mRNA and protein expression and TNF-induced DNA binding of NF-κB proteins, and inhibits the TNF-induced nuclear entry of activated NF-κB proteins thereby inhibiting inflammatory gene activation (Loewe et al., J Immunology 2002, 168, $478_{1-4}787$). TNF signaling pathways are implicated in the pathogenesis of immune-mediated inflammatory diseases such as rheumatoid arthritis, Crohn's disease, psoriasis, psoriatic arthritis, juvenile idiopathic arthritis, and ankylosing spondylitis (Tracey et al., Pharmacology & Therapeutics 2008, 117, 244-279).

Fumaderm®, an enteric coated tablet containing a salt mixture of monomethyl fumarate and dimethylfumarate (DMF) (A-2) which is rapidly hydrolyzed to monomethyl fumarate (MHF) (A-1), regarded as the main bioactive metabolite, was approved in Germany in 1994 for the treatment of psoriasis.

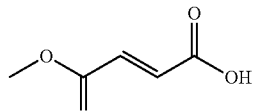

(A-1)

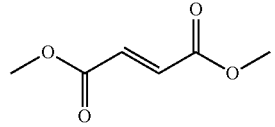

(A-2)

Fumaderm® is dosed TID with 1-2 grams/day administered for the treatment of psoriasis. Fumaderm® exhibits a high degree of interpatient variability with respect to drug absorption and food strongly reduces bioavailability. Absorption is thought to occur in the small intestine with peak levels achieved 5-6 hours after oral administration. Significant side effects occur in 70-90% of patients (Brewer and Rogers, Clin Expt'l Dermatology 2007, 32, 246-49; and Hoefnagel et al., Br J Dermatology 2003, 149, 363-369). Side effects of current FAE therapy include gastrointestinal upset including nausea, vomiting, and diarrhea; transient flushing of the skin. Also, DMF exhibits poor aqueous solubility.

Fumaric acid derivatives (Flachsmann et al., U.S. Pat. No. 7,638,118 (morpholino esters); Gangakhedkar et al., U.S. Pat. No. 8,148,414 (glycolamide esters) and U.S. Pat. No. 8,778, 991 (acyloxyalkyl esters); Joshi and Strebel, WO 2002/ 055063, US 2006/0205659, and U.S. Pat. No. 7,157,423 (amide compounds and protein-fumarate conjugates); Joshi et al., WO 2002/055066 and Joshi and Strebel, U.S. Pat. No. 6,355,676 (mono and dialkyl esters); Joshi and Strebel, WO 2003/087174 (carbocyclic and oxacarbocylic compounds); Joshi et al., WO 2006/122652 (thiosuccinates); Joshi et al., US 2008/0233185 (dialkyl and diaryl esters); Zeidan et al., U.S. Pat. No. 8,669,281 (pyrrolidine esters)) and salts (Nilsson et al., US 2008/0004344) have been developed in an effort to overcome the deficiencies of current FAE therapy. Controlled release pharmaceutical compositions comprising fumaric acid esters are disclosed by Nilsson and Müller, WO 2007/042034. Glycolamide ester prodrugs are described by Nielsen and Bundgaard, J Pharm Sci 1988, 77(4), 285-298.

SUMMARY

Fumarate compounds having high gastrointestinal permeability and/or absorption, improved solubility, ordered hydrolysis (i.e., preferential cleavage of promoieties), and minimal cleavage in the gut lumen or enterocyte cytoplasm are desirable. Such fumarates, which provide higher oral bioavailability and plasma levels of the parent compound, an alkyl hydrogen fumarate, e.g., MHF, and/or other metabolites of the fumarates, may: enhance the efficacy/responder rate compared to present fumaric acid esters; facilitate the use of lower doses, reduce dosing frequency, and standardize dosing regimens; reduce food effects; reduce gastrointestinal side effects/toxicity; and reduce interpatient treatment variability.

In a first aspect, compounds of Formula (I) are provided:

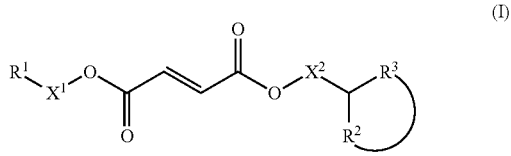

or a pharmaceutically acceptable salt thereof, wherein:

$R^1$ is chosen from hydrogen, $C_{1-6}$ alkyl, substituted $C_{1-6}$ alkyl, $C_{1-6}$ heteroalkyl, substituted $C_{1-6}$ heteroalkyl, $C_{3-12}$ cycloalkyl, substituted $C_{3-12}$ cycloalkyl, $C_{3-12}$ heterocycloalkyl, substituted $C_{3-12}$ heterocycloalkyl, $C_{5-10}$ aryl, substituted $C_{5-10}$ aryl, $C_{5-10}$ heteroaryl, and substituted $C_{5-10}$ heteroaryl;

$R^2$ and $R^3$ together with the carbon to which they are bonded form a ring chosen from $C_{5-10}$ heteroaryl and substituted $C_{5-10}$ heteroaryl; and $X^1$ and $X^2$ are independently chosen from a bond and $C_{1-6}$ alkane-diyl;

wherein each substituent group is independently chosen from halogen, —OH, —CN, —CF$_3$, =O, —NO$_2$, benzyl, —C(O)NR$^{21}_2$, —R$^{21}$, —OR$^{21}$, —C(O)R$^{21}$, —C(O)OR$^{21}$, —NR$^{21}_2$, —NR$^{21}$C(O)R$^{21}$, and —O(O)R$^{21}$, wherein each $R^{21}$ is independently chosen from hydrogen, $C_{1-6}$ alkyl, $C_{1-6}$ heteroalkyl, $C_{3-12}$ cycloalkyl, $C_{5-10}$ aryl, $C_{5-10}$ heteroaryl, and amino acid side chain.

In a second aspect, pharmaceutical compositions are provided comprising a compound of Formula (I) and at least one pharmaceutically acceptable vehicle.

In a third aspect, methods of treating a disease in a patient are provided comprising administering to a patient in need of such treatment a pharmaceutical composition comprising a therapeutically effective amount of a compound of Formula (I). In certain embodiments, the disease is chosen from a neurodegenerative disease, an inflammatory disease, and an autoimmune disease including, for example, multiple sclerosis, psoriasis, irritable bowel disorder, ulcerative colitis, arthritis, chronic obstructive pulmonary disease, asthma, Parkinson's disease, Huntington's disease, and amyotrophic lateral sclerosis.

DETAILED DESCRIPTION

Definitions

A dash ("-") that is not between two letters or symbols is used to indicate a point of attachment for a moiety or substituent. For example, —CONH$_2$ is bonded through the carbon atom.

"Alkyl" refers to a saturated or unsaturated, branched, or straight-chain, monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having combinations of single, double, and triple carbon-carbon bonds. Where a specific level of saturation is intended, the terms alkanyl, alkenyl, and alkynyl are used. In certain embodiments, an alkyl group can have from 1 to 20 carbon atoms ($C_{1-20}$) in certain embodiments, from 1 to 10 carbon atoms ($C_{1-10}$), in certain embodiments from 1 to 8 carbon atoms ($C_{1-8}$), in certain embodiments, from 1 to 6 carbon atoms ($C_{1-6}$), in certain embodiments from 1 to 4 carbon atoms ($C_{1-4}$), and in certain embodiments, from 1 to 3 carbon atoms ($C_{1-3}$).

"Alkane-diyl" refers to a diradical of a saturated or unsaturated, branched, or straight-chain acyclic hydrocarbon group, having, for example, from 1 to 20 carbon atoms, from 1-10 carbon atoms, from 1-6 carbon atoms, from 1 to 4 carbon atoms, or from 1 to 3 hydrocarbon atoms. Examples of alkane-diyl groups include methane-diyl (—CH$_2$—), ethane-1,2-diyl (—CH$_2$CH$_2$—), propane-1,3-diyl and iso-propane-1,2-diyl (e.g., —CH$_2$CH$_2$CH$_2$— and —CH(CH$_3$)CH$_2$—), butane-1,4-diyl (—CH$_2$CH$_2$CH$_2$CH$_2$—), pentane-1,5-diyl (—CH$_2$CH$_2$CH$_2$CH$_2$CH$_2$—), hexane-1,6-diyl (—CH$_2$CH$_2$CH$_2$CH$_2$CH$_2$CH$_2$—), heptane-1,7-diyl, octane-1,8-diyl, nonane-1,9-diyl, decane-1,10-diyl, dodecane-1,12-diyl, and the like.

"Amino acid side chain" includes the side chains of naturally occurring standard amino acids, side chains of naturally occurring non-standard amino acids, and side chains of non-naturally occurring amino acid derivatives. In certain embodiments the amino acid side chain is selected from a hydrogen, methyl, isopropyl, sec-butyl, phenyl, benzyl, p-hydroxybenzyl, —CH₂OH, —CH₂CH₂OH, —CH(OH)CH₃, —CH₂CH₂SCH₃, —CH₂CONH₂, —CH₂COOH, —CH₂CH₂CONH₂, —CH₂CH₂COOH, —(CH₂)₃NHC(=NH)NH₂, —(CH₂)₃NH₂, —(CH₂)₃NHCOCH₃, —(CH₂)₃NHCHO, —(CH₂)₄NHC(=NH)NH₂, —(CH₂)₄NH₂, —(CH₂)₄NHCOCH₃, —(CH₂)₄NHCHO, —(CH₂)₃NHCONH₂, —(CH₂)₄NHCONH₂, —CH₂CH₂CH(OH)CH₂NH₂,

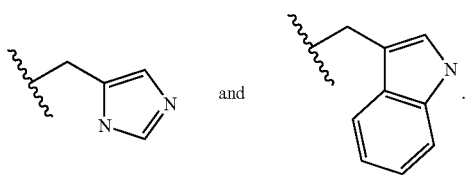 [SMILES: *Cc1cnc[nH]1 ; *Cc1c[nH]c2ccccc12]

In certain embodiments the amino acid side chain is bonded to a chiral carbon atom that is in the (R) configuration, and in certain embodiments, the (S) configuration.

"Arene-diyl" refers to an aromatic hydrocarbon diradical derived by the removal of two hydrogen atoms from a single carbon atom or by the removal of a single hydrogen atom from two carbon atoms of a parent aromatic ring system. In certain embodiments, an arene-diyl group is $C_{5-20}$ arene-diyl, $C_{5-12}$ arene-diyl, $C_{5-10}$ arene-diyl, and in certain embodiments, $C_{5-8}$ arene-diyl. Examples of arene-diyl groups include benzene-1,2-diyl, benzene-1,3-diyl, benzene-1,4-diyl, naphthalene-1,6-diyl, and the like.

"Aryl" refers to a monovalent aromatic hydrocarbon radical derived by the removal of one hydrogen atom from a single carbon atom of a parent aromatic ring system. Aryl benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms chosen from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can have from 6 to 20 carbon atoms ($C_{6-20}$), from 6 to 12 carbon atoms ($C_{6-12}$), from 6 to 10 carbon atoms ($C_{6-10}$), and in certain embodiments from 6 to 8 carbon atoms ($C_{6-8}$). Aryl, however, does not encompass or overlap in any way with heteroaryl, separately defined herein.

"Compounds" of Formula (I) disclosed herein include any specific compounds within the formula. Compounds may be identified either by their chemical structure and/or chemical name. Compounds are named using Accelrys Draw 4.1 SP1, version MDL.Draw.Editor 4.1. 100.70 (Accelrys, Inc., San Diego, Calif.). When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan. Compounds of Formula (I) include, but are not limited to, optical isomers of compounds of Formula (I), racemates thereof, and other mixtures thereof. In such embodiments, a single enantiomer or diastereomer, i.e., optically active form can be obtained by asymmetric synthesis or by resolution of the racemates. Resolution of the racemates may be accomplished, for example, by conventional methods such as crystallization in the presence of a resolving agent, or chromatography using, for example, chiral stationary phases. Not withstanding the foregoing, in compounds of Formula (I) the configuration of the illustrated double bond is only in the E configuration (i.e. trans configuration).

Compounds of Formula (I) may also exist in several tautomeric forms including the enol form, the keto form, and mixtures thereof. Accordingly, the chemical structures depicted herein encompass all possible tautomeric forms of the illustrated compounds. Compounds of Formula (I) also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds may exist in unsolvated forms as well as solvated forms, including hydrated forms and as N-oxides. In general, compounds as referred to herein may be free acid, hydrated, solvated, or N-oxides. Certain compounds may exist in multiple crystalline, co-crystalline, or amorphous forms. Compounds of Formula (I) include pharmaceutically acceptable salts thereof, or pharmaceutically acceptable solvates of the free acid form of any of the foregoing, as well as crystalline forms of any of the foregoing.

Compounds of Formula (I) also include solvates. A solvate refers to a molecular complex of a compound with one or more solvent molecules in a stoichiometric or non-stoichiometric amount. Such solvent molecules are those commonly used in the pharmaceutical art, which are known to be innocuous to a patient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water.

Further, when partial structures of the compounds are illustrated, an asterisk (*) or a wavy line (⁓⁓⁓⁓) indicates the point of attachment of the partial structure to the rest of the molecule.

"Cycloalkyl" refers to a saturated or partially unsaturated cyclic alkyl radical. Where a specific level of saturation is intended, the nomenclature cycloalkanyl or cycloalkenyl is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, $C_{3-12}$ cycloalkyl, and in certain embodiments, $C_{3-8}$ cycloalkyl.

"Cycloalkane-diyl" refers to a diradical cyclic or polycyclic hydrocarbon group. In certain embodiments, a cycloalkane-diyl group is $C_{3-12}$ cycloalkane-diyl, $C_{3-8}$ cycloalkane-diyl, $C_{3-6}$ cycloalkane-diyl, and in certain embodiments, $C_{5-6}$ cycloalkane-diyl. Examples of cycloalkane-diyl groups include cyclohexane-1,4-diyl, cyclohexane-1,3-diyl, and cyclohexane-1,2-diyl.

"Disease" refers to a disease, disorder, condition, or symptom of any of the foregoing.

"Drug" as defined under 21 U.S.C. §321(g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals . . . ."

"Halogen" refers to a fluoro, chloro, bromo, or iodo group. In certain embodiments, halogen refers to a chloro group.

"Heteroalkyl" by itself or as part of another substituent refers to an alkyl group in which one or more of the carbon atoms (and certain associated hydrogen atoms) are independently replaced with the same or different heteroatomic groups. Examples of heteroatomic groups include, but are not limited to, —O—, —S—, —O—O—, —S—S—, —O—S—, —NR$^{91}$—, =N—N=, —N=N—, —N=N—NR$^{91}$—, —PR$^{91}$—, —P(O)$_2$—, —POR$^{91}$—, —O—P(O)$_2$—, —SO—, —SO$_2$—, —Sn(R$^{91}$)$_2$—, and the like, where each R$^{91}$ is independently chosen from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, or substituted $C_{7-18}$ heteroarylalkyl. Reference to, for example, a $C_{1-6}$ heteroalkyl, means a $C_{1-6}$ alkyl group in which at least one of the carbon atoms (and certain associated hydrogen atoms) is replaced with a heteroatom. For example $C_{1-6}$ heteroalkyl includes groups having five carbon atoms and one heteroatom, groups having four carbon atoms and two heteroatoms, etc. In certain embodiments, each R$^{91}$ is independently chosen from hydrogen and $C_{1-3}$ alkyl. In certain embodiments, a heteroatomic group is chosen from —O—, —S—, —NH—, —N(CH$_3$)—, and —SO$_2$—; and in certain embodiments, the heteroatomic group is —O—.

"Heteroalkane-diyl" refers to an alkane-diyl group wherein one or more of the carbon atoms are replaced with a heteroatom (e.g., N, O, S, P, or Si).

"Heteroarene-diyl" refers to an arene-diyl group wherein one or more of the carbon atoms are replaced with a heteroatom (e.g., N, O, S, P, or Si). Examples of heteroarene-diyl groups include furane-diyl and pyridine-diyl.

"Heteroaryl" by itself or as part of another substituent refers to a aryl group in which one or more of the carbon atoms (and certain associated hydrogen atoms) are independently replaced with the same or different heteroatomic groups. Examples of heteroatomic groups include, but are not limited to, —O—, —S—, —O—O—, —S—S—, —O—S—, —NR$^{91}$—, =N—N=, —N=N—, —N=N—NR$^{91}$—, —PR$^{91}$—, —P(O)$_2$—, —POR$^{91}$—, —O—P(O)$_2$—, —SO—, —SO$_2$—, —Sn(R$^{91}$)$_2$—, and the like, where each R$^{91}$ is independently chosen from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, or substituted $C_{7-18}$ heteroarylalkyl.

Heteroaryl encompasses multiple ring systems having at least one heteroaromatic ring fused to at least one other ring, which can be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like. In certain embodiments, a heteroaryl group is from 4- to 20-membered heteroaryl ($C_{4-20}$), and in certain embodiments from 4- to 12-membered heteroaryl ($C_{4-10}$). In certain embodiments, heteroaryl groups are those derived from thiophene, pyrrole, benzothiophene, benzofuran, indole, pyridine, quinoline, imidazole, oxazole, or pyrazine. For example, in certain embodiments, $C_5$ heteroaryl can be furyl, thienyl, pyrrolyl, imidazolyl, pyrazolyl, isothiazolyl, and isoxazolyl.

"Heterocycloalkane-diyl" by itself or as part of another substituent refers to a cycloalkane-diyl group in which one or more of the carbon atoms (and certain associated hydrogen atoms) are independently replaced with the same or different heteroatomic groups. Examples of heteroatomic groups include, but are not limited to, —O—, —S—, —O—O—, —S—S—, —O—S—, —NR$^{91}$—, =N—N=, —N=N—, —N=N—NR$^{91}$—, —PR$^{91}$—, —P(O)$_2$—, —POR$^{91}$—, —O—P(O)$_2$—, —SO—, —SO$_2$—, —Sn(R$^{91}$)$_2$—, and the like, where each R$^{91}$ is independently chosen from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, or substituted $C_{7-18}$ heteroarylalkyl. Reference to, for example, a $C_{3-6}$ heterocycloalkane-diyl, means a $C_{3-6}$ cycloalkane-diyl group in which at least one of the carbon atoms (and certain associated hydrogen atoms) is replaced with a heteroatom. For example $C_{3-6}$ heterocycloalkane-diyl includes groups having five carbon atoms and one heteroatom, groups having four carbon atoms and two heteroatoms, etc. In certain embodiments, each R$^{91}$ is independently chosen from hydrogen and $C_{1-3}$ alkyl. In certain embodiments, a heteroatomic group is chosen from —O—, —S—, —NH—, —N(CH$_3$)—, and —SO$_2$—; and in certain embodiments, the heteroatomic group is —O—.

"Heterocycloalkyl" by itself or as part of another substituent refers to a cycloalkyl group in which one or more of the carbon atoms (and certain associated hydrogen atoms) are independently replaced with the same or different heteroatomic groups. Examples of heteroatomic groups include, but are not limited to, —O—, —S—, —O—O—, —S—S—, —O—S—, —NR$^{91}$, =N—N=, —N=N—, —N=N—NR$^{91}$—, —PR$^{91}$—, —P(O)$_2$—, —POR$^{91}$—, —O—P(O)$_2$—, —SO—, —SO$_2$—, —Sn(R$^{91}$)$_2$—, and the like, where each R$^{91}$ is independently chosen from hydrogen, C$_{1-6}$ alkyl, substituted C$_{1-6}$ alkyl, C$_{6-12}$ aryl, substituted C$_{6-12}$ aryl, C$_{7-18}$ arylalkyl, substituted C$_{7-18}$ arylalkyl, C$_{3-7}$ cycloalkyl, substituted C$_{3-7}$ cycloalkyl, C$_{3-7}$ heterocycloalkyl, substituted C$_{3-7}$ heterocycloalkyl, C$_{1-6}$ heteroalkyl, substituted C$_{1-6}$ heteroalkyl, C$_{6-12}$ heteroaryl, substituted C$_{6-12}$ heteroaryl, C$_{7-18}$ heteroarylalkyl, or substituted C$_{7-18}$ heteroarylalkyl. Reference to, for example, a C$_{3-6}$ heterocycloalkyl, means a C$_{3-6}$ cycloalkyl group in which at least one of the carbon atoms (and certain associated hydrogen atoms) is replaced with a heteroatom. For example C$_{3-6}$ heterocycloalkyl includes groups having five carbon atoms and one heteroatom, groups having four carbon atoms and two heteroatoms, etc. In certain embodiments, each R$^{91}$ is independently chosen from hydrogen and C$_{1-3}$ alkyl. In certain embodiments, a heteroatomic group is chosen from —O—, —S—, —NH—, —N(CH$_3$)—, and —SO$_2$—; and in certain embodiments, the heteroatomic group is —O—.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to an aromatic ring system in which one or more carbon atoms (and any associated hydrogen atoms) are independently replaced with the same or different heteroatom in such a way as to maintain the continuous 71-electron system characteristic of aromatic systems and a number of out-of-plane ii-electrons corresponding to the Hückel rule (4n+2). Examples of heteroatoms to replace the carbon atoms include, but are not limited to, N, P, O, S, and Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt. In certain embodiments, a pharmaceutically acceptable salt is the sodium salt.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound of Formula (I) and at least one pharmaceutically acceptable vehicle, with which the compound of Formula (I) is administered to a patient.

"Substituted" refers to a group in which one or more hydrogen atoms are independently replaced with the same or substituent group(s). In certain embodiments, each substituent group is independently chosen from halogen, —OH, —CN, —CF$_3$, =O, —NO$_2$, benzyl, —C(O)NR$^{21}$$_2$, —R$^{21}$, —OR$^{21}$, —C(O)R$^{21}$, —COOR$^{21}$, —C(R$^{21}$)NH$_2$, —C(O)C(R$^{21}$)NH$_2$, —C(R$^{21}$)C(O)OH, —NC(R$^{21}$)C(O)OH, —NR$^{21}$$_2$, —NR$^{21}$C(O)R$^{21}$, and —O(O)R$^{21}$, wherein each R$^{21}$ is independently chosen from hydrogen, C$_{1-6}$ alkyl, C$_{1-6}$ heteroalkyl, C$_{3-12}$ cycloalkyl, C$_{5-10}$ aryl, C$_{5-10}$ heteroaryl, and amino acid side chain. In certain embodiments, each substituent group is independently chosen from halogen, —OH, —CN, —CF$_3$, —NO$_2$, benzyl, —R$^{21}$, —OR$^{21}$, —C(O)R$^{21}$, —COOR$^{21}$, —C(R$^{21}$)NH$_2$, —C(O)C(R$^{21}$)NH$_2$, —C(R$^{21}$)C(O)OH, —NC(R$^{21}$)C(O)OH, —NR$^{21}$$_2$, —NR$^{21}$C(O)R$^{21}$, and —O(O)R$^{21}$, wherein each R$^{21}$ is independently chosen from hydrogen, C$_{1-6}$ alkyl, C$_{1-6}$ heteroalkyl, C$_{3-12}$ cycloalkyl, C$_{5-10}$ aryl, C$_{5-10}$ heteroaryl, and amino acid side chain. In certain embodiments, each substituent group is independently chosen from halogen, —OH, —CN, —CF$_3$, =O, —NO$_2$, benzyl, —C(O)NR$^{21}$$_2$, —R$^{21}$, —OR$^{21}$, —C(O)R$^{21}$, —COOR$^{21}$, —NR$^{21}$$_2$, —NR$^{21}$C(O)R$^{21}$, and —O(O)R$^{21}$, wherein each R$^{21}$ is independently chosen from hydrogen, C$_{1-6}$ alkyl, C$_{1-6}$ heteroalkyl, C$_{3-12}$ cycloalkyl, C$_{5-10}$ aryl, C$_{5-10}$ heteroaryl, and amino acid side chain. In certain embodiments, each substituent group is independently chosen from —OH, —NH$_2$, C$_{1-4}$ alkyl, and amino acid side chain. In certain embodiments, each substituent group is independently chosen from —OH, —C(O)NR$^{21}_2$, —R$^{21}$, —C(O)R$^{21}$, —COOR$^{21}$, —C(R$^{21}$)NH$_2$, —C(O)C(R$^{21}$)NH$_2$, —C(R$^{21}$)C(O)OH, and —NC(R$^{21}$)C(O)OH, wherein each R$^{21}$ is independently chosen from a hydrogen, methyl, isopropyl, sec-butyl, phenyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$,

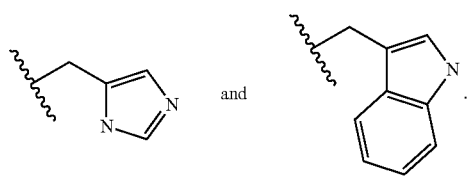 [SMILES: *Cc1cnc[nH]1 ; *Cc1c[nH]c2ccccc12]

and

"Treating" or "treatment" of any disease refers to reversing, alleviating, arresting, or ameliorating a disease or at least one of the clinical symptoms of a disease, reducing the risk of acquiring a disease or at least one of the clinical symptoms of a disease, inhibiting the progress of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter that may or may not be discernible to the patient. In certain embodiments, "treating" or "treatment" refers to delaying the onset of the disease or at least one or more symptoms thereof in a patient which may be exposed to or predisposed to a disease even though that patient does not yet experience or display symptoms of the disease.

"Therapeutically effective amount" refers to the amount of a compound that, when administered to a subject for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

Reference is now made in detail to certain embodiments of compounds, compositions, and methods. The disclosed embodiments are not intended to be limiting of the claims. To the contrary, the claims are intended to cover all alternatives, modifications, and equivalents.

Compounds

Certain embodiments provide a compound of Formula (I):

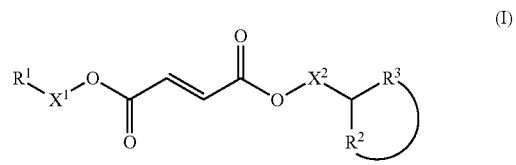

(I)

or a pharmaceutically acceptable salt thereof, wherein:

R$^1$ is chosen from hydrogen, C$_{1-6}$ alkyl, substituted C$_{1-6}$ alkyl, C$_{1-6}$ heteroalkyl, substituted C$_{1-6}$ heteroalkyl, C$_{3-12}$ cycloalkyl, substituted C$_{3-12}$ cycloalkyl, C$_{3-12}$ heterocycloalkyl, substituted C$_{3-12}$ heterocycloalkyl, C$_{5-10}$ aryl, substituted C$_{5-10}$ aryl, C$_{5-10}$ heteroaryl, and substituted C$_{5-10}$ heteroaryl;

R$^2$ and R$^3$ together with the carbon to which they are bonded form a ring chosen from C$_{5-10}$ heteroaryl and substituted C$_{5-10}$ heteroaryl; and X$^1$ and X$^2$ are independently chosen from a bond and C$_{1-6}$ alkane-diyl;

wherein each substituent group is independently chosen from halogen, —OH, —CN, —CF$_3$, =O, —NO$_2$, benzyl, —C(O)NR$^{21}_2$, —R$^{21}$, —OR$^{21}$, —C(O)R$^{21}$, —C(O)OR$^{21}$, —NR$^{21}_2$, —NR$^{21}$C(O)R$^{21}$, and —O(O)R$^{21}$, wherein each R$^{21}$ is independently chosen from hydrogen, C$_{1-6}$ alkyl, C$_{1-6}$ heteroalkyl, C$_{3-12}$ cycloalkyl, C$_{5-10}$ aryl, C$_{5-10}$ heteroaryl, and amino acid side chain.

In certain embodiments of a compound of Formula (I), each substituent group is independently chosen from halogen, —OH, —CN, —CF$_3$, =O, —NO$_2$, benzyl, —C(O)NR$^{21}_2$, —R$^{21}$, —OR$^{21}$, —C(O)R$^{21}$, —C(O)OR$^{21}$, —NR$^{21}_2$, —NR$^{21}$C(O)R$^{21}$, and —O(O)R$^{21}$, wherein each R$^{21}$ is independently chosen from hydrogen, C$_{1-6}$ alkyl, C$_{1-6}$ heteroalkyl, C$_{3-12}$ cycloalkyl, C$_{5-10}$ aryl, C$_{5-10}$ heteroaryl, and amino acid side chain.

In certain embodiments of a compound of Formula (I), each substituent group is independently chosen from fluoro, chloro, —OH, —OCH$_3$, —C(O)CH$_3$, —NH$_2$, —N(CH$_3$)$_2$, —C(O)OH, —C(O)OCH$_3$, —C(O)OCH$_2$CH$_3$, —C(O)NH$_2$, —C(O)NH$_2$, —C(O)NHCH$_3$, —C(O)N(CH$_3$)$_2$, —C(R$^{21}$)NH$_2$, —C(R$^{21}$)C(O)OH, —NHC(O)R$^{21}$, and —O(O)R$^{21}$, wherein each R$^{21}$ is chosen from hydrogen, C$_{1-6}$ alkyl, C$_{1-6}$ heteroalkyl, C$_{3-12}$ cycloalkyl, C$_{5-10}$ aryl, and C$_{5-10}$ heteroaryl.

In certain embodiments of a compound of Formula (I), each substituent group is independently chosen from methyl, ethyl, n-propyl, isopropyl, n-butyl, isobutyl, sec-butyl, and tert-butyl.

In certain embodiments of a compound of Formula (I), each substituent group is independently chosen from fluoro, chloro, —OH, —OCH$_3$, —C(O)CH$_3$, —C(O)CH$_2$CH$_3$, —C(O)CH(CH$_3$)$_2$, —C(O)Ph, —NH$_2$, —N(CH$_3$)$_2$, —N(CH$_2$CH$_2$OCH$_3$)$_2$, —C(O)OH, —C(O)OCH$_3$, —C(O)OCH$_2$CH$_3$, —C(O)NH$_2$, —C(O)NH$_2$, —C(O)NHCH$_3$, —C(O)N(CH$_3$)$_2$, —C(R$^{21}$)NH$_2$, —C(R$^{21}$)C(O)OH, —NHC(O)R$^{21}$, and —O(O)R$^{21}$, wherein each R$^{21}$ is independently chosen from hydrogen, C$_{1-6}$ alkyl, C$_{1-6}$ heteroalkyl, C$_{3-12}$ cycloalkyl, C$_{5-10}$ aryl, and C$_{5-10}$ heteroaryl.

In certain embodiments of a compound of Formula (I), each substituent group is independently chosen from —NR²¹C(O)R²¹ and —O(O)R²¹, wherein each R²¹ is independently chosen from hydrogen, methyl, ethyl, n-propyl, isopropyl, n-butyl, isobutyl, sec-butyl, tert-butyl, cyclohexyl, phenyl, and benzyl.

In certain embodiments of a compound of Formula (I), each substituent group is independently chosen from fluoro, chloro, —OH, —OCH₃, —C(O)CH₃, —NH₂, —N(CH₃)₂, —N(CH₂CH₂OCH₃)₂, —C(O)OH, —C(O)OCH₃, —C(O)OCH₂CH₃, —C(O)OCH(CH₃)₂, —C(O)NH₂, —C(O)NHCH₃, —C(O)NH(CH₂CH₃), —C(O)N(CH₃)₂, —C(O)N(CH₂CH₃)₂, —NHC(O)CH₃, —NHC(O)CH(CH₃)₂, —NHC(O)Ph, —OC(O)CH₃, —OC(O)CH₂CH₃, —OC(O)CH(CH₃)₂, —OC(O)C(CH₃)₃, and —OC(O)Ph.

In certain embodiments of a compound of Formula (I), each substituent group is independently chosen from methyl, isopropyl, sec-butyl, phenyl, benzyl, p-hydroxybenzyl, —CH₂OH, —CH₂CH₂OH, —CH(OH)CH₃, —CH₂OCH₃, —CH₂CH₂OCH₃, —CH₂CH₂CH₂OCH₃, and —CH₂CH₂CH₂OCH₂CH₃.

In certain embodiments of a compound of Formula (I), R¹ is chosen from hydrogen, $C_{1-6}$ alkyl, substituted $C_{1-6}$ alkyl, $C_{1-6}$ heteroalkyl, substituted $C_{1-6}$ heteroalkyl, $C_{3-12}$ cycloalkyl, substituted $C_{3-12}$ cycloalkyl, $C_{3-12}$ heterocycloalkyl, substituted $C_{3-12}$ heterocycloalkyl, $C_{5-10}$ aryl, substituted $C_{5-10}$ aryl, $C_{5-10}$ heteroaryl, and substituted $C_{5-10}$ heteroaryl.

In certain embodiments of a compound of Formula (I), R¹ is chosen from hydrogen and $C_{1-6}$ alkyl.

In certain embodiments of a compound of Formula (I), R¹ is chosen from hydrogen, methyl, ethyl, n-propyl, isopropyl, n-butyl, isobutyl, tert-butyl, n-pentyl, pentyl-2-yl, 2-methylbutyl, isopentyl, 3-methylbutan-2-yl, neopentyl, tert-pentyl, n-hexyl, hexan-2-yl, 2-methylpentyl, 3-methylpentyl, 4-methylpentyl, 3-methylpentan-2-yl, 4-methylpentan-2-yl, 2,3-dimethylbutyl, and 3,3-dimethylbutyl.

In certain embodiments of a compound of Formula (I), R¹ is chosen from hydrogen and substituted $C_{1-6}$ alkyl.

In certain embodiments of a compound of Formula (I), R¹ is chosen from hydrogen, substituted methyl, substituted ethyl, substituted n-propyl, substituted isopropyl, substituted n-butyl, substituted isobutyl, substituted tert-butyl, substituted n-pentyl, substituted pentyl-2-yl, substituted 2-methylbutyl, substituted isopentyl, substituted 3-methylbutan-2-yl, substituted neopentyl, substituted tert-pentyl, substituted n-hexyl, substituted hexan-2-yl, substituted 2-methylpentyl, substituted 3-methylpentyl, substituted 4-methylpentyl, substituted 3-methylpentan-2-yl, substituted 4-methylpentan-2-yl, substituted 2,3-dimethylbutyl, substituted and substituted 3,3-dimethylbutyl, wherein each substituent group is independently chosen from halogen, —OH, —CN, —CF₃, =O, —NO₂, benzyl, —C(O)NR²¹₂, —R²¹, —OR²¹, —C(O)R²¹, —C(O)OR²¹, —NR²¹₂, —NR²¹C(O)R²¹, and —O(O)R²¹, wherein each R²¹ is independently chosen from hydrogen, $C_{1-6}$ alkyl, $C_{1-6}$ heteroalkyl, $C_{3-12}$ cycloalkyl, $C_{5-10}$ aryl, $C_{5-10}$ heteroaryl, and amino acid side chain.

In certain embodiments of a compound of Formula (I), R¹ is chosen from hydrogen, acetoxymethyl; benzoyloxymethyl; cyclohexanecarbonyloxymethyl; 2,2-dimethylpropanoyloxymethyl; 1-(2-methylpropanoyloxy)ethyl; 2-methylpropanoyloxymethyl; and propanoyloxymethyl.

In certain embodiments of a compound of Formula (I), R¹ is chosen from hydrogen and $C_{1-6}$ heteroalkyl.

In certain embodiments of a compound of Formula (I), R¹ is chosen from hydrogen, methoxymethyl, 2-methoxyethyl, 2-ethoxyethyl, 3-methoxypropyl, 3-ethoxypropyl, and 4-methoxybutyl.

In certain embodiments of a compound of Formula (I), R¹ is chosen from hydrogen and substituted $C_{1-6}$ heteroalkyl.

In certain embodiments of a compound of Formula (I), R¹ is chosen from hydrogen, substituted methoxymethyl, substituted 2-methoxyethyl, substituted 2-ethoxyethyl, substituted 3-methoxypropyl, substituted 3-ethoxypropyl, and substituted 4-methoxybutyl, wherein each substituent group is independently chosen from halogen, —OH, —CN, —CF₃, =O, —NO₂, benzyl, —C(O)NR²¹₂, —R²¹, —OR²¹, —C(O)R²¹, —C(O)OR²¹, —NR²¹₂, —NR²¹C(O)R²¹, and —O(O)R²¹, wherein each R²¹ is independently chosen from hydrogen, $C_{1-6}$ alkyl, $C_{1-6}$ heteroalkyl, $C_{3-12}$ cycloalkyl, $C_{5-10}$ aryl, $C_{5-10}$ heteroaryl, and amino acid side chain.

In certain embodiments of a compound of Formula (I), R¹ is chosen from hydrogen and $C_{3-12}$ cycloalkyl.

In certain embodiments of a compound of Formula (I), R¹ is chosen from hydrogen, cyclopropyl, cyclobutyl, cyclopentyl, cyclohexyl, cycloheptyl, and cyclooctyl.

In certain embodiments of a compound of Formula (I), R¹ is chosen from hydrogen and substituted $C_{3-12}$ cycloalkyl.

In certain embodiments of a compound of Formula (I), R¹ is chosen from hydrogen, substituted cyclopropyl, substituted cyclobutyl, substituted cyclopentyl, substituted cyclohexyl, substituted cycloheptyl, and substituted cyclooctyl, wherein each substituent group is independently chosen from halogen, —OH, —CN, —CF₃, =O, —NO₂, benzyl, —C(O)NR²¹₂, —R²¹, —OR²¹, —C(O)R²¹, —C(O)OR²¹, —NR²¹₂, —NR²¹C(O)R²¹, and —O(O)R²¹, wherein each R²¹ is independently chosen from hydrogen, $C_{1-6}$ alkyl, $C_{1-6}$ heteroalkyl, $C_{3-12}$ cycloalkyl, $C_{5-10}$ aryl, $C_{5-10}$ heteroaryl, and amino acid side chain.

In certain embodiments of a compound of Formula (I), R¹ is chosen from hydrogen and $C_{3-12}$ heterocycloalkyl.

In certain embodiments of a compound of Formula (I), R¹ is chosen from hydrogen; azepan-1-yl; azetidin-1-yl; 2H-azet-1-yl; aziridin-1-yl; azirin-1-yl; azocan-1-yl; 1,2-dihydroimidazol-3-yl; 2,4-dihydroimidazol-3-yl; 4,5-dihydroimidazol-1-yl; 1,3-dihydropyrazol-2-yl; 1,5-dihydropyrazol-2-yl; 3,4-dihydropyrazol-2-yl; 2,3-dihydropyrrol-1-yl; 2,5-dihydropyrrol-1-yl; 1,5-dihydro-1,2,4-triazol-4-yl; 3,5-dihydro-1,2,4-triazol-4-yl; 4,5-dihydrotriazol-1-yl; 1,3,5-dioxazinan-5-yl; 1,3,2-dioxazol-2-yl; hexahydropyrimidin-1-yl; imidazolidin-1-yl; morpholin-4-yl; 1,3-oxazetidin-3-yl; oxazetidin-2-yl; 1,3-oxazinan-3-yl; oxazolidin-3-yl; 2H-oxazol-3-yl; piperazin-1-yl; 1-piperidyl; pyrazolidin-1-yl; and pyrrolidin-1-yl.

In certain embodiments of a compound of Formula (I), R¹ is chosen from hydrogen, morpholin-4-yl; oxazolidin-3-yl; 1-piperidyl; pyrrolidin-1-yl; 2,5-dioxopyrrolidin-1-yl; and 2-oxopyrrolidin-1-yl.

In certain embodiments of a compound of Formula (I), R¹ is chosen from hydrogen and morpholin-4-yl.

In certain embodiments of a compound of Formula (I), R¹ is chosen from hydrogen and substituted $C_{3-12}$ heterocycloalkyl.

In certain embodiments of a compound of Formula (I), R¹ is chosen from hydrogen; substituted azepan-1-yl; substituted azetidin-1-yl; substituted 2H-azet-1-yl; substituted aziridin-1-yl; substituted azirin-1-yl; substituted azocan-1-yl; substituted 1,2-dihydroimidazol-3-yl; substituted 2,4-dihydroimidazol-3-yl; substituted 4,5-dihydroimidazol-1-yl; substituted 1,3-dihydropyrazol-2-yl; substituted 1,5-dihydropyrazol-2-yl; substituted 3,4-dihydropyrazol-2-yl; substituted 2,3-dihydropyrrol-1-yl; substituted 2,5-dihydropyrrol-1-yl; substituted 1,5-dihydro-1,2,4-triazol-4-yl; substituted 3,5-dihydro-1,2,4-triazol-4-yl; substituted 4,5-dihydrotriazol-1-yl; substituted 1,3,5-dioxazinan-5-yl; substituted 1,3,2-dioxazol-2-yl; substituted hexahydropyrimidin-1-yl; substituted imidazolidin-1-yl; substituted morpholin-4-yl; substituted 1,3-oxazetidin-3-yl; substituted oxazetidin-2-yl; substituted 1,3-oxazinan-3-yl; substituted oxazolidin-3-yl; substituted 2H-oxazol-3-yl; substituted piperazin-1-yl; substituted 1-piperidyl; substituted pyrazolidin-1-yl; and substituted pyrrolidin-1-yl; wherein each substituent group is independently chosen from halogen, —OH, —CN, —CF$_3$, =O, —NO$_2$, benzyl, —C(O)NR$^{21}$$_2$, —R$^{21}$, —OR$^{21}$, —C(O)R$^{21}$, —C(O)OR$^{21}$, —NR$^{21}$$_2$, —NR$^{21}$C(O)R$^{21}$, and —O(O)R$^{21}$, wherein each R$^{21}$ is independently chosen from hydrogen, C$_{1-6}$ alkyl, C$_{1-6}$ heteroalkyl, C$_{3-12}$ cycloalkyl, C$_{5-10}$ aryl, C$_{5-10}$ heteroaryl, and amino acid side chain.

In certain embodiments of a compound of Formula (I), R$^1$ is chosen from hydrogen; (4-amino-2-oxo-pyrimidin-1-yl); [(2R)-2-carboxypyrrolidin-1-yl]; (2,5-dioxopiperazin-1-yl); (2,6-dioxo-1-piperidyl); (2,4-dioxopyrimidin-1-yl); (2,5-dioxopyrrolidin-1-yl); (2,5-dioxopyrrol-1-yl); (5-methyl-2,4-dioxo-pyrimidin-1-yl); 1,3,4-oxadiazin-4-yl; 1,4-oxazin-4-yl; oxazin-2-yl; (2-oxoazetidin-1-yl); (3-oxoazetidin-1-yl); (2-oxomorpholin-4-yl); (2-oxo-1-piperidyl); (3-oxo-1-piperidyl); (4-oxo-1-piperidyl); (2-oxopyrrolidin-1-yl); (3-oxopyrrolidin-1-yl); and (5-methyl-2-oxo-1,3-dioxol-4-yl)methyl.

In certain embodiments of a compound of Formula (I), R$^1$ is chosen from hydrogen and C$_{5-10}$ aryl.

In certain embodiments of a compound of Formula (I), R$^1$ is chosen from hydrogen, phenyl, phenylphenyl, and naphthyl.

In certain embodiments of a compound of Formula (I), R$^1$ is chosen from hydrogen and substituted C$_{5-10}$ aryl.

In certain embodiments of a compound of Formula (I), R$^1$ is chosen from hydrogen, substituted phenyl, substituted phenylphenyl, and substituted naphthyl, wherein each substituent group is independently chosen from halogen, —OH, —CN, —CF$_3$, =O, —NO$_2$, benzyl, —C(O)NR$^{21}$$_2$, —R$^{21}$, —OR$^{21}$, —C(O)R$^{21}$, —C(O)OR$^{21}$, —NR$^{21}$$_2$, —NR$^{21}$C(O)R$^{21}$, and —O(O)R$^{21}$, wherein each R$^{21}$ is independently chosen from hydrogen, C$_{1-6}$ alkyl, C$_{1-6}$ heteroalkyl, C$_{3-12}$ cycloalkyl, C$_{5-10}$ aryl, C$_{5-10}$ heteroaryl, and amino acid side chain.

In certain embodiments of a compound of Formula (I), R$^1$ is chosen from hydrogen and C$_{5-10}$ heteroaryl.

In certain embodiments of a compound of Formula (I), R$^1$ is chosen from hydrogen; furyl; imidazol-yl; indol-yl; isoxazol-yl; oxazol-yl; pyrazin-yl; pyridyl; pyrimidin-yl; pyrrol-yl; tetrazol-yl; thienyl; and triazol-yl.

In certain embodiments of a compound of Formula (I), R$^1$ is chosen from hydrogen; 2-furyl; 3-furyl; 1H-imidazol-2-yl; 1H-imidazol-4-yl; 1H-indol-2-yl; 1H-indol-3-yl; 1H-indol-4-yl; 1H-indol-5-yl; 1H-indol-6-yl; 1H-indol-7-yl; isoxazol-3-yl; isoxazol-4-yl; isoxazol-5-yl; oxazol-2-yl; oxazol-4-yl; oxazol-5-yl; pyrazin-2-yl; 2-pyridyl; 3-pyridyl; 4-pyridyl; pyrimidin-2-yl; pyrimidin-4-yl; pyrimidin-5-yl; 1H-pyrrol-2-yl; 1H-pyrrol-3-yl; 2H-pyrrol-2-yl; 2H-pyrrol-3-yl; 1H-tetrazol-5-yl; 2-thienyl; 3-thienyl; 1H-triazol-4-yl; and 4H-1,2,4-triazol-3-yl.

In certain embodiments of a compound of Formula (I), R$^1$ is chosen from hydrogen; benzimidazol-1-yl; benzotriazol-1-yl; 1,2,4-benzoxadiazin-2-yl; 1,4-benzoxazin-4-yl; carbazol-9-yl; imidazol-1-yl; indazol-1-yl; indolin-1-yl; indol-1-yl; isoindolin-2-yl; phenoxazin-10-yl; purin-7-yl; purin-9-yl; pyrazol-1-yl; pyrrol-1-yl; tetrazol-1-yl; triazol-1-yl; and 1,2,4-triazol-4-yl.

In certain embodiments of a compound of Formula (I), R$^1$ is chosen from hydrogen; indol-1-yl; purin-7-yl; purin-9-yl; and 1,2,4-triazol-4-yl.

In certain embodiments of a compound of Formula (I), R$^1$ is chosen from hydrogen and substituted C$_{5-10}$ heteroaryl ring.

In certain embodiments of a compound of Formula (I), R$^1$ is chosen from hydrogen; substituted furyl; substituted imidazol-yl; substituted indol-yl; substituted isoxazol-yl; substituted oxazol-yl; substituted pyrazin-yl; substituted pyridyl; substituted pyrimidin-yl; substituted pyrrol-yl; substituted tetrazol-yl; substituted thienyl; and substituted triazol-yl; wherein each substituent group is independently chosen from halogen, —OH, —CN, —CF$_3$, =O, —NO$_2$, benzyl, —C(O)NR$^{21}$$_2$, —R$^{21}$, —OR$^{21}$, —C(O)R$^{21}$, —C(O)OR$^{21}$, —NR$^{21}$$_2$, —NR$^{21}$C(O)R$^{21}$, and —O(O)R$^{21}$, wherein each R$^{21}$ is independently chosen from hydrogen, C$_{1-6}$ alkyl, C$_{1-6}$ heteroalkyl, C$_{3-12}$ cycloalkyl, C$_{5-10}$ aryl, C$_{5-10}$ heteroaryl, and amino acid side chain.

In certain embodiments of a compound of Formula (I), R$^1$ is chosen from hydrogen; substituted 2-furyl; substituted 3-furyl; substituted 1H-imidazol-2-yl; substituted 1H-imidazol-4-yl; substituted 1H-indol-2-yl; substituted 1H-indol-3-yl; substituted 1H-indol-4-yl; substituted 1H-indol-5-yl; substituted 1H-indol-6-yl; substituted 1H-indol-7-yl; substituted isoxazol-3-yl; substituted isoxazol-4-yl; substituted isoxazol-5-yl; substituted oxazol-2-yl; substituted oxazol-4-yl; substituted oxazol-5-yl; substituted pyrazin-2-yl; substituted 2-pyridyl; substituted 3-pyridyl; substituted 4-pyridyl; substituted pyrimidin-2-yl; substituted pyrimidin-4-yl; substituted pyrimidin-5-yl; substituted 1H-pyrrol-2-yl; substituted 1H-pyrrol-3-yl; substituted 2H-pyrrol-2-yl; substituted 2H-pyrrol-3-yl; substituted 1H-tetrazol-5-yl; substituted 2-thienyl; substituted 3-thienyl; substituted 1H-triazol-4-yl; and substituted 4H-1,2,4-triazol-3-yl; wherein each substituent group is independently chosen from halogen, —OH, —CN, —CF$_3$, =O, —NO$_2$, benzyl, —C(O)NR$^{21}$$_2$, —R$^{21}$, —OR$^{21}$, —C(O)R$^{21}$, —C(O)OR$^{21}$, —NR$^{21}$$_2$, —NR$^{21}$C(O)R$^{21}$, and —O(O)R$^{21}$, wherein each R$^{21}$ is independently chosen from hydrogen, C$_{1-6}$ alkyl, C$_{1-6}$ heteroalkyl, C$_{3-12}$ cycloalkyl, C$_{5-10}$ aryl, C$_{5-10}$ heteroaryl, and amino acid side chain.

In certain embodiments of a compound of Formula (I), R$^1$ is chosen from hydrogen; substituted benzimidazol-1-yl; substituted benzotriazol-1-yl; substituted 1,2,4-benzoxadiazin-2-yl; substituted 1,4-benzoxazin-4-yl; substituted carbazol-9-yl; substituted imidazol-1-yl; substituted indazol-1-yl; substituted indolin-1-yl; substituted indol-1-yl; substituted isoindolin-2-yl; substituted phenoxazin-10-yl; substituted purin-7-yl; substituted purin-9-yl; substituted pyrazol-1-yl; substituted pyrrol-1-yl; substituted tetrazol-1-yl; substituted triazol-1-yl; and substituted 1,2,4-triazol-4-yl; wherein each substituent group is independently chosen from halogen, —OH, —CN, —CH$_3$, —CF$_3$, =O, —NH$_2$, —NO$_2$, —C(O)NH$_2$, —OCH$_3$, —C(O)H, and —C(O)OH.

In certain embodiments of a compound of Formula (I), R$^1$ is chosen from hydrogen; (2-amino-6-oxo-1H-purin-9-yl); (6-aminopurin-9-yl); (2,3-dioxoindolin-1-yl); (1,3-dioxoisoindolin-2-yl); (2-oxoindolin-1-yl); and (1-oxoisoindolin-2-yl).

In certain embodiments of a compound of Formula (I), R$^1$ is (5-methyl-2-oxo-1,3-dioxol-4-yl)methyl. In certain embodiments of a compound of Formula (I), R$^1$ is 2-methylpropanoyloxymethyl. In certain embodiments of a compound of Formula (I), R$^1$ is phenyl. In certain embodiments of a compound of Formula (I), R$^1$ is benzyl. In certain embodiments of a compound of Formula (I), R$^1$ is isopropyl. In certain embodiments of a compound of Formula (I), R$^1$ is ethyl. In certain embodiments of a compound of Formula (I), R$^1$ is methyl. In certain embodiments of a compound of Formula (I), $R^1$ is morpholin-4-yl. In certain embodiments of a compound of Formula (I), $R^1$ is 1,2,4-triazol-4-yl. In certain embodiments of a compound of Formula (I), $R^1$ is hydrogen.

In certain embodiments of a compound of Formula (I), $R^1$ is chosen from hydrogen; methyl; ethyl; n-propyl; isopropyl; n-butyl; tert-butyl; phenyl; benzyl; (1,3-dioxoisoindolin-2-yl); (2,5-dioxopyrrolidin-1-yl); (2,5-dioxopyrrol-1-yl); indol-1-yl; morpholin-4-yl; 1,3-oxazinan-3-yl; oxazolidin-3-yl; (1-oxoisoindolin-2-yl); (2-oxomorpholin-4-yl); (4-oxo-1-piperidyl); (2-oxopyrrolidin-1-yl); (3-oxopyrrolidin-1-yl); 1-piperidyl; tetrazol-1-yl; triazol-1-yl; 1,2,4-triazol-4-yl; 1-benzoyloxyethyl; benzoyloxymethyl; (1,3-dimethyl-2,5-dioxo-imidazolidin-4-yl); (1,3-dimethyl-2-oxo-imidazolidin-4-yl); (2,5-dioxoimidazolidin-4-yl); (2,5-dioxopyrrolidin-3-yl); (1-methyl-2,5-dioxo-imidazolidin-4-yl); (3-methyl-2,5-dioxo-imidazolidin-4-yl); (1-methyl-2,5-dioxo-pyrrolidin-3-yl); (5-methyl-2-oxo-1,3-dioxol-4-yl)methyl; (3-methyl-2-oxo-oxazolidin-4-yl); (3-methyl-2-oxo-oxazolidin-5-yl); (1-methyl-2-oxo-pyrrolidin-3-yl); (1-methyl-5-oxo-pyrrolidin-2-yl); (1-methyl-5-oxo-pyrrolidin-3-yl); 1-(2-methylpropanoyloxy)ethyl; 2-methylpropanoyloxymethyl; (2-oxoimidazolidin-4-yl); (2-oxooxazolidin-4-yl); (2-oxooxazolidin-5-yl); (2-oxopyrrolidin-3-yl); (5-oxopyrrolidin-2-yl); and (5-oxopyrrolidin-3-yl).

In certain embodiments of a compound of Formula (I), $R^1$ is ethyl. In certain embodiments of a compound of Formula (I), $R^1$ is methyl. In certain embodiments of a compound of Formula (I), $R^1$ is morpholin-4-yl. In certain embodiments of a compound of Formula (I), $R^1$ is 1,2,4-triazol-4-yl. In certain embodiments of a compound of Formula (I), $R^1$ is hydrogen.

In certain embodiments of a compound of Formula (I), $R^2$ and $R^3$ together with the carbon to which they are bonded form a ring chosen from $C_{5-10}$ heteroaryl and substituted $C_{5-10}$ heteroaryl.

In certain embodiments of a compound of Formula (I), $R^2$ and $R^3$ together with the carbon to which they are bonded form a $C_{5-10}$ heteroaryl ring.

In certain embodiments of a compound of Formula (I), $R^2$ and $R^3$ together with the carbon to which they are bonded form a substituted $C_{5-10}$ heteroaryl ring, wherein each substituent group is independently chosen from halogen, —OH, —CN, —CF$_3$, =O, —NO$_2$, benzyl, —C(O)NR$^{21}_2$, —R$^{21}$, —OR$^{21}$, —C(O)R$^{21}$, —C(O)OR$^2$, —NR$^{21}_2$, —NR$^{21}$C(O)R$^{21}$, and —O(O)R$^{21}$, wherein each $R^{21}$ is independently chosen from hydrogen, $C_{1-6}$ alkyl, $C_{1-6}$ heteroalkyl, $C_{3-12}$ cycloalkyl, $C_{5-10}$ aryl, $C_{5-10}$ heteroaryl, and amino acid side chain.

In certain embodiments of a compound of Formula (I), $R^2$ and $R^3$ together with the carbon to which they are bonded form a ring chosen from pyrimidinyl, substituted pyrimidinyl, purinyl, and substituted purinyl.

In certain embodiments of a compound of Formula (I), $R^2$ and $R^3$ together with the carbon to which they are bonded form a ring chosen from (2,4-dioxo-1H-pyrimidin-5-yl) and (2,4-dioxo-1H-pyrimidin-5-yl)methyl.

In certain embodiments of a compound of Formula (I), $R^2$ and $R^3$ together with the carbon to which they are bonded form a ring chosen from (2,4-dioxo-1H-pyrimidin-6-yl) and (2,4-dioxo-1H-pyrimidin-6-yl)methyl.

In certain embodiments of a compound of Formula (I), $X^1$ and $X^2$ are independently chosen from a bond and $C_{1-6}$ alkane-diyl.

In certain embodiments of a compound of Formula (I), $X^1$ and $X^2$ are independently chosen from a bond; methane-diyl; ethane-1,1-diyl; ethane-1,2-diyl; propane-1,2-diyl; propane-1,3-diyl; 2-methylpropane-1,2-diyl; 2,2-dimethylpropane-1,3-diyl; butane-1,2-diyl; butane-1,3-diyl; butane-1,4-diyl; butane-2,3-diyl; 2,3-dimethylbutane-2,3-diyl; pentane-1,5-diyl; and hexane-1,6-diyl.

In certain embodiments of a compound of Formula (I), $X^1$ and $X^2$ are independently chosen from a bond; methane-diyl; ethane-1,1-diyl; ethane-1,2-diyl; propane-1,2-diyl; propane-1,3-diyl; 2-methylpropane-1,2-diyl; 2,2-dimethylpropane-1,3-diyl; and hexane-1,6-diyl.

In certain embodiments of a compound of Formula (I), $X^1$ and $X^2$ are independently chosen from a bond; methane-diyl; ethane-1,2-diyl; propane-1,3-diyl; 2,2-dimethylpropane-1,3-diyl; and hexane-1,6-diyl.

In certain embodiments of a compound of Formula (I), $X^1$ and $X^2$ are independently chosen from a bond; methane-diyl; ethane-1,2-diyl; and propane-1,3-diyl.

In certain embodiments of a compound of Formula (I), $X^1$ is a bond. In certain embodiments of a compound of Formula (I), $X^1$ is methane-diyl. In certain embodiments of a compound of Formula (I), $X^1$ is ethane-1,2-diyl. In certain embodiments of a compound of Formula (I), $X^1$ is propane-1,3-diyl.

In certain embodiments of a compound of Formula (I), $X^2$ is a bond. In certain embodiments of a compound of Formula (I), $X^2$ is methane-diyl. In certain embodiments of a compound of Formula (I), $X^2$ is ethane-1,2-diyl. In certain embodiments of a compound of Formula (I), $X^2$ is propane-1,3-diyl.

In certain embodiments of a compound of Formula (I), $X^2$ is methane-diyl.

In certain embodiments of a compound of Formula (I), $R^1$ is chosen from hydrogen, $C_{1-6}$ alkyl, $C_{1-6}$ heteroalkyl, $C_{3-12}$ cycloalkyl, $C_{3-12}$ heterocycloalkyl, $C_{5-10}$ aryl, and $C_{5-10}$ heteroaryl; $R^2$ and $R^3$ together with the carbon to which they are bonded form a ring chosen from $C_{5-10}$ heteroaryl and substituted $C_{5-10}$ heteroaryl; and $X^1$ and $X^2$ are independently chosen from a bond and $C_{1-6}$ alkane-diyl; wherein each substituent group is independently chosen from halogen, —OH, —CN, —CF$_3$, =O, —NO$_2$, benzyl, —C(O)NR$^{21}_2$, —R$^{21}$, —OR$^{21}$, —C(O)R$^{21}$, —C(O)OR$^{21}$, —NR$^{21}_2$, —NR$^{21}$C(O)R$^{21}$, and —O(O)R$^{21}$, wherein each $R^{21}$ is independently chosen from hydrogen, $C_{1-6}$ alkyl, $C_{1-6}$ heteroalkyl, $C_{3-12}$ cycloalkyl, $C_{5-10}$ aryl, $C_{5-10}$ heteroaryl, and amino acid side chain.

In certain embodiments of a compound of Formula (I), $R^1$ is chosen from hydrogen, methyl, ethyl, n-propyl, isopropyl, n-butyl, tert-butyl, phenyl, benzyl, (1,3-dioxoisoindolin-2-yl), (2,5-dioxopyrrolidin-1-yl), (2,5-dioxopyrrol-1-yl), indol-1-yl, morpholin-4-yl, 1,3-oxazinan-3-yl, oxazolidin-3-yl, (1-oxoisoindolin-2-yl), (2-oxomorpholin-4-yl), (4-oxo-1-piperidyl), (2-oxopyrrolidin-1-yl), (3-oxopyrrolidin-1-yl), 1-piperidyl, tetrazol-1-yl, triazol-1-yl, 1,2,4-triazol-4-yl, 1-benzoyloxyethyl, benzoyloxymethyl, (1,3-dimethyl-2,5-dioxo-imidazolidin-4-yl), (1,3-dimethyl-2-oxo-imidazolidin-4-yl), (2,5-dioxoimidazolidin-4-yl), (2,5-dioxopyrrolidin-3-yl), (1-methyl-2,5-dioxo-imidazolidin-4-yl), (3-methyl-2,5-dioxo-imidazolidin-4-yl), (1-methyl-2,5-dioxo-pyrrolidin-3-yl), (5-methyl-2-oxo-1,3-dioxol-4-yl)methyl, (3-methyl-2-oxo-oxazolidin-4-yl), (3-methyl-2-oxo-oxazolidin-5-yl), (1-methyl-2-oxo-pyrrolidin-3-yl), (1-methyl-5-oxo-pyrrolidin-2-yl), (1-methyl-5-oxo-pyrrolidin-3-yl), 1-(2-methylpropanoyloxy)ethyl, 2-methylpropanoyloxymethyl, (2-oxoimidazolidin-4-yl), (2-oxooxazolidin-4-yl), (2-oxooxazolidin-5-yl), (2-oxopyrrolidin-3-yl), (5-oxopyrrolidin-2-yl), and (5-oxopyrrolidin-3-yl); $R^2$ and $R^3$ together with the carbon to which they are bonded form a ring chosen from pyrimidinyl, substituted pyrimidinyl, purinyl, and substituted purinyl; and $X^1$ and $X^2$ are independently chosen from a bond, methane-diyl, ethane-1,1-diyl, ethane-1,2-diyl, propane-1,2-diyl, propane-1,3-diyl, 2-methylpropane-1,2-diyl, 2,2-dimethylpropane-1,3-diyl, butane-1,2-diyl, butane-1,3-diyl, butane-1,4-diyl, butane-2,3-diyl, 2,3-dimethylbutane-2,3-diyl, pentane-1,5-diyl, and hexane-1,6-diyl; wherein each substituent group is independently chosen from halogen, —OH, —CN, —CF$_3$, =O, —NO$_2$, benzyl, —C(O)NR$^{21}$$_2$, —R$^{21}$, —OR$^{21}$, —C(O)R$^{21}$, —C(O)OR$^{21}$, —NR$^{21}$$_2$, —NR$^{21}$C(O)R$^{21}$, and —O(O)R$^{21}$, wherein each R$^{21}$ is independently chosen from hydrogen, C$_{1-6}$ alkyl, C$_{1-6}$ heteroalkyl, C$_{3-12}$ cycloalkyl, C$_{5-10}$ aryl, C$_{5-10}$ heteroaryl, and amino acid side chain.

In certain embodiments of a compound of Formula (I), R$^1$ is chosen from hydrogen, methyl, ethyl, n-propyl, isopropyl, n-butyl, tert-butyl, phenyl, benzyl, (1,3-dioxoisoindolin-2-yl), (2,5-dioxopyrrolidin-1-yl), (2,5-dioxopyrrol-1-yl), indol-1-yl, morpholin-4-yl, 1,3-oxazinan-3-yl, oxazolidin-3-yl, (1-oxoisoindolin-2-yl), (2-oxomorpholin-4-yl), (4-oxo-1-piperidyl), (2-oxopyrrolidin-1-yl), (3-oxopyrrolidin-1-yl), 1-piperidyl, tetrazol-1-yl, triazol-1-yl, 1,2,4-triazol-4-yl, 1-benzoyloxyethyl, benzoyloxymethyl, (1,3-dimethyl-2,5-dioxo-imidazolidin-4-yl), (1,3-dimethyl-2-oxo-imidazolidin-4-yl), (2,5-dioxoimidazolidin-4-yl), (2,5-dioxopyrrolidin-3-yl), (1-methyl-2,5-dioxo-imidazolidin-4-yl), (3-methyl-2,5-dioxo-imidazolidin-4-yl), (1-methyl-2,5-dioxo-pyrrolidin-3-yl), (5-methyl-2-oxo-1,3-dioxol-4-yl)methyl, (3-methyl-2-oxo-oxazolidin-4-yl), (3-methyl-2-oxo-oxazolidin-5-yl), (1-methyl-2-oxo-pyrrolidin-3-yl), (1-methyl-5-oxo-pyrrolidin-2-yl), (1-methyl-5-oxo-pyrrolidin-3-yl), 1-(2-methylpropanoyloxy)ethyl, 2-methylpropanoyloxymethyl, (2-oxoimidazolidin-4-yl), (2-oxooxazolidin-4-yl), (2-oxooxazolidin-5-yl), (2-oxopyrrolidin-3-yl), (5-oxopyrrolidin-2-yl), and (5-oxopyrrolidin-3-yl); R$^2$ and R$^3$ together with the carbon to which they are bonded form a ring chosen from (2,4-dioxo-1H-pyrimidin-5-yl) and (2,4-dioxo-1H-pyrimidin-5-yl)methyl; and X$^1$ and X$^2$ are independently chosen from a bond, methane-diyl, ethane-1,1-diyl, ethane-1,2-diyl, propane-1,2-diyl, propane-1,3-diyl, 2-methylpropane-1,2-diyl, 2,2-dimethylpropane-1,3-diyl, butane-1,2-diyl, butane-1,3-diyl, butane-1,4-diyl, butane-2,3-diyl, 2,3-dimethylbutane-2,3-diyl, pentane-1,5-diyl, and hexane-1,6-diyl.

In certain embodiments of a compound of Formula (I), R$^1$ is chosen from hydrogen, methyl, ethyl, n-propyl, isopropyl, n-butyl, tert-butyl, phenyl, and benzyl; R$^2$ and R$^3$ together with the carbon to which they are bonded form a ring chosen from (2,4-dioxo-1H-pyrimidin-5-yl) and (2,4-dioxo-1H-pyrimidin-5-yl)methyl; and X$^1$ and X$^2$ are independently chosen from a bond, methane-diyl, ethane-1,1-diyl, ethane-1,2-diyl, propane-1,2-diyl, propane-1,3-diyl, 2-methylpropane-1,2-diyl, 2,2-dimethylpropane-1,3-diyl, butane-1,2-diyl, butane-1,3-diyl, butane-1,4-diyl, butane-2,3-diyl, 2,3-dimethylbutane-2,3-diyl, pentane-1,5-diyl, and hexane-1,6-diyl.

In certain embodiments of a compound of Formula (I), R$^1$ is chosen from hydrogen, methyl, ethyl, n-propyl, isopropyl, n-butyl, tert-butyl, phenyl, and benzyl; R$^2$ and R$^3$ together with the carbon to which they are bonded form a ring chosen from (2,4-dioxo-1H-pyrimidin-5-yl) and (2,4-dioxo-1H-pyrimidin-5-yl)methyl; and X$^1$ and X$^2$ are independently chosen from a bond, methane-diyl, ethane-1,1-diyl, ethane-1,2-diyl, and propane-1,3-diyl.

In certain embodiments of a compound of Formula (I), R$^1$ is hydrogen; R$^2$ and R$^3$ together with the carbon to which they are bonded form a (2,4-dioxo-1H-pyrimidin-5-yl) ring; X$^1$ is a bond; and X$^2$ is a bond.

In certain embodiments of a compound of Formula (I), R$^1$ is methyl; R$^2$ and R$^3$ together with the carbon to which they are bonded form a (2,4-dioxo-1H-pyrimidin-5-yl) ring; X$^1$ is a bond; and X$^2$ is a bond.

In certain embodiments of a compound of Formula (I), R$^1$ is ethyl; R$^2$ and R$^3$ together with the carbon to which they are bonded form a (2,4-dioxo-1H-pyrimidin-5-yl) ring; X$^1$ is a bond; and X$^2$ is a bond.

In certain embodiments of a compound of Formula (I), R$^1$ is isopropyl; R$^2$ and R$^3$ together with the carbon to which they are bonded form a (2,4-dioxo-1H-pyrimidin-5-yl) ring; X$^1$ is a bond; and X$^2$ is a bond.

In certain embodiments of a compound of Formula (I), R$^1$ is isobutyl; R$^2$ and R$^3$ together with the carbon to which they are bonded form a (2,4-dioxo-1H-pyrimidin-5-yl) ring; X$^1$ is a bond; and X$^2$ is a bond.

In certain embodiments of a compound of Formula (I), R$^1$ is sec-butyl; R$^2$ and R$^3$ together with the carbon to which they are bonded form a (2,4-dioxo-1H-pyrimidin-5-yl) ring; X$^1$ is a bond; and X$^2$ is a bond.

In certain embodiments of a compound of Formula (I), R$^1$ is tert-butyl; R$^2$ and R$^3$ together with the carbon to which they are bonded form a (2,4-dioxo-1H-pyrimidin-5-yl) ring; X$^1$ is a bond; and X$^2$ is a bond.

In certain embodiments of a compound of Formula (I), R$^1$ is phenyl; R$^2$ and R$^3$ together with the carbon to which they are bonded form a (2,4-dioxo-1H-pyrimidin-5-yl) ring; X$^1$ is a bond; and X$^2$ is a bond.

In certain embodiments of a compound of Formula (I), R$^1$ is benzyl; R$^2$ and R$^3$ together with the carbon to which they are bonded form a (2,4-dioxo-1H-pyrimidin-5-yl) ring; X$^1$ is a bond; and X$^2$ is a bond.

In certain embodiments of a compound of Formula (I), R$^1$ is morpholin-4-yl; R$^2$ and R$^3$ together with the carbon to which they are bonded form a (2,4-dioxo-1H-pyrimidin-5-yl) ring; X$^1$ is butane-1,4-diyl; and X$^2$ is a bond.

In certain embodiments of a compound of Formula (I), R$^1$ is (5-methyl-2-oxo-1,3-dioxol-4-yl)methyl; R$^2$ and R$^3$ together with the carbon to which they are bonded form a (2,4-dioxo-1H-pyrimidin-5-yl) ring; X$^1$ is a bond; and X$^2$ is a bond.

In certain embodiments of a compound of Formula (I), R$^1$ is 2-methylpropanoyloxymethyl; R$^2$ and R$^3$ together with the carbon to which they are bonded form a (2,4-dioxo-1H-pyrimidin-5-yl) ring; X$^1$ is a bond; and X$^2$ is a bond.

In certain embodiments of a compound of Formula (I), R$^1$ is (2,4-dioxo-1H-pyrimidin-5-yl); R$^2$ and R$^3$ together with the carbon to which they are bonded form a (2,4-dioxo-1H-pyrimidin-5-yl) ring; X$^1$ is a bond; and X$^2$ is a bond.

In certain embodiments of a compound of Formula (I), R$^1$ is hydrogen; R$^2$ and R$^3$ together with the carbon to which they are bonded form a (2,4-dioxo-1H-pyrimidin-5-yl) ring; X$^1$ is a bond; and X$^2$ is methane-diyl.

In certain embodiments of a compound of Formula (I), R$^1$ is methyl; R$^2$ and R$^3$ together with the carbon to which they are bonded form a (2,4-dioxo-1H-pyrimidin-5-yl) ring; X$^1$ is a bond; and X$^2$ is methane-diyl.

In certain embodiments of a compound of Formula (I), $R^1$ is ethyl; $R^2$ and $R^3$ together with the carbon to which they are bonded form a (2,4-dioxo-1H-pyrimidin-5-yl) ring; $X^1$ is a bond; and $X^2$ is methane-diyl.

In certain embodiments of a compound of Formula (I), $R^1$ is isopropyl; $R^2$ and $R^3$ together with the carbon to which they are bonded form a (2,4-dioxo-1H-pyrimidin-5-yl) ring; $X^1$ is a bond; and $X^2$ is methane-diyl.

In certain embodiments of a compound of Formula (I), $R^1$ is isobutyl; $R^2$ and $R^3$ together with the carbon to which they are bonded form a (2,4-dioxo-1H-pyrimidin-5-yl) ring; $X^1$ is a bond; and $X^2$ is methane-diyl.

In certain embodiments of a compound of Formula (I), $R^1$ is sec-butyl; $R^2$ and $R^3$ together with the carbon to which they are bonded form a (2,4-dioxo-1H-pyrimidin-5-yl) ring; $X^1$ is a bond; and $X^2$ is methane-diyl.

In certain embodiments of a compound of Formula (I), $R^1$ is tert-butyl; $R^2$ and $R^3$ together with the carbon to which they are bonded form a (2,4-dioxo-1H-pyrimidin-5-yl) ring; $X^1$ is a bond; and $X^2$ is methane-diyl.

In certain embodiments of a compound of Formula (I), $R^1$ is phenyl; $R^2$ and $R^3$ together with the carbon to which they are bonded form a (2,4-dioxo-1H-pyrimidin-5-yl) ring; $X^1$ is a bond; and $X^2$ is methane-diyl.

In certain embodiments of a compound of Formula (I), $R^1$ is benzyl; $R^2$ and $R^3$ together with the carbon to which they are bonded form a (2,4-dioxo-1H-pyrimidin-5-yl) ring; $X^1$ is a bond; and $X^2$ is methane-diyl.

In certain embodiments of a compound of Formula (I), $R^1$ is morpholin-4-yl; $R^2$ and $R^3$ together with the carbon to which they are bonded form a (2,4-dioxo-1H-pyrimidin-5-yl) ring; $X^1$ is butane-1,4-diyl; and $X^2$ is methane-diyl.

In certain embodiments of a compound of Formula (I), $R^1$ is (5-methyl-2-oxo-1,3-dioxol-4-yl)methyl; $R^2$ and $R^3$ together with the carbon to which they are bonded form a (2,4-dioxo-1H-pyrimidin-5-yl) ring; $X^1$ is a bond; and $X^2$ is methane-diyl.

In certain embodiments of a compound of Formula (I), $R^1$ is 2-methylpropanoyloxymethyl; $R^2$ and $R^3$ together with the carbon to which they are bonded form a (2,4-dioxo-1H-pyrimidin-5-yl) ring; $X^1$ is a bond; and $X^2$ is methane-diyl.

In certain embodiments of a compound of Formula (I), $R^1$ is (2,4-dioxo-1H-pyrimidin-5-yl); $R^2$ and $R^3$ together with the carbon to which they are bonded form a (2,4-dioxo-1H-pyrimidin-5-yl) ring; $X^1$ is methane-diyl; and $X^2$ is methane-diyl.

In certain embodiments of a compound of Formula (I), the compound is chosen from a compound of Formula (I-A-1), Formula (I-A-2), Formula (I-A-3), Formula (I-A-4), Formula (I-A-5), Formula (I-A-6), Formula (I-A-7), Formula (I-A-8), Formula (I-A-9), Formula (I-A-10), Formula (I-A-11), and Formula (I-A-12), or a pharmaceutically acceptable salt of any of the foregoing:

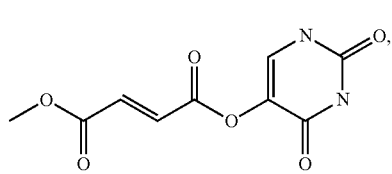
(I-A-1)

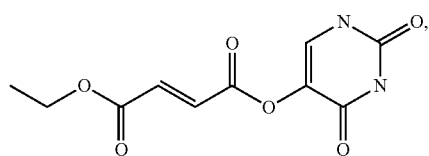
(I-A-2)

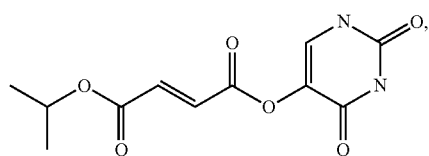
(I-A-3)

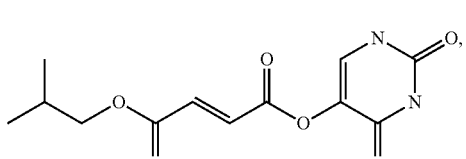
(I-A-4)

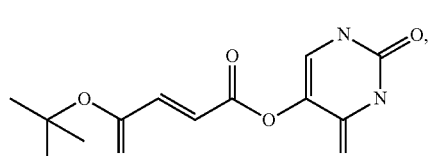
(I-A-5)

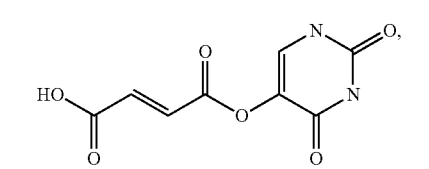
(I-A-6)

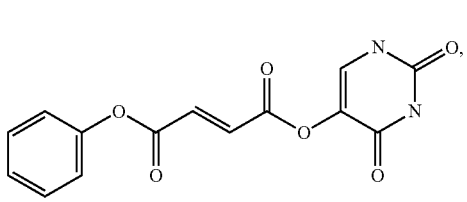
(I-A-7)

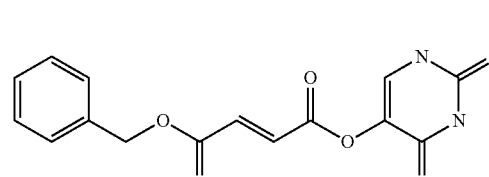
(I-A-8)

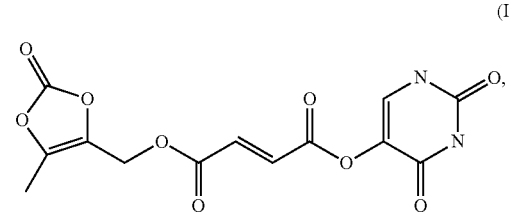
(I-A-9)

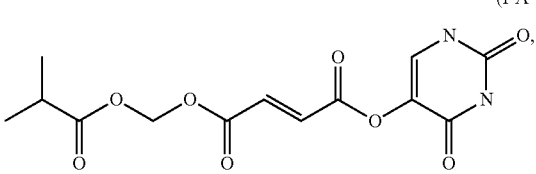
(I-A-10)

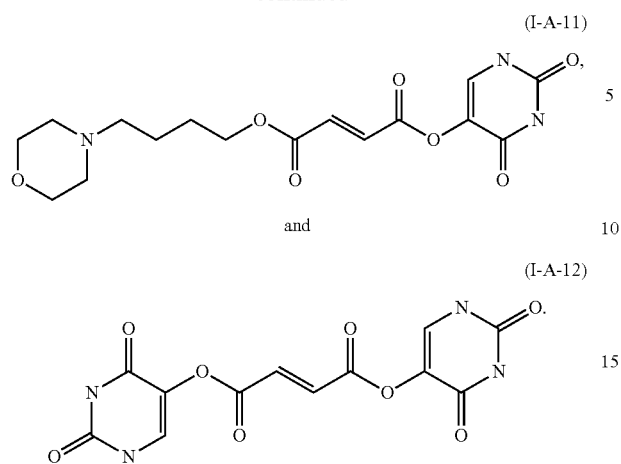

In certain embodiments of a compound of Formula (I), the compound is chosen from a compound of Formula (I-B-1), Formula (I-B-2), Formula (I-B-3), Formula (I-B-4), Formula (I-B-5), Formula (I-B-6), Formula (I-B-7), Formula (I-B-8), Formula (I-B-9), Formula (I-B-10), Formula (I-B-1), and Formula (I-B-12), or a pharmaceutically acceptable salt of any of the foregoing:

In certain embodiments of a compound of Formula (I), the compound is chosen from a compound of Formula (I-C-1), Formula (I-C-2), Formula (I-C-3), Formula (I-C-4), Formula (I-C-5), Formula (I-C-6), Formula (I-C-7), Formula (I-C-8), Formula (I-C-9), Formula (I-C-10), Formula (I-C-11), and Formula (I-C-12), or a pharmaceutically acceptable salt of any of the foregoing:

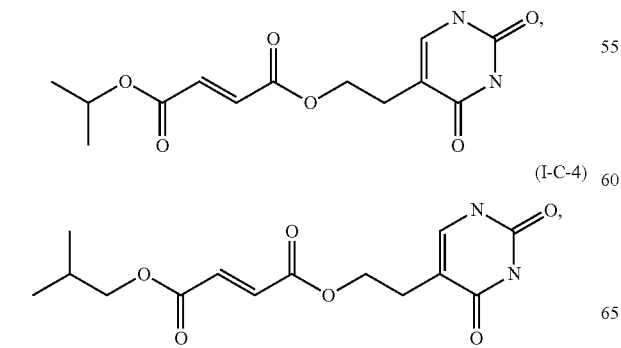

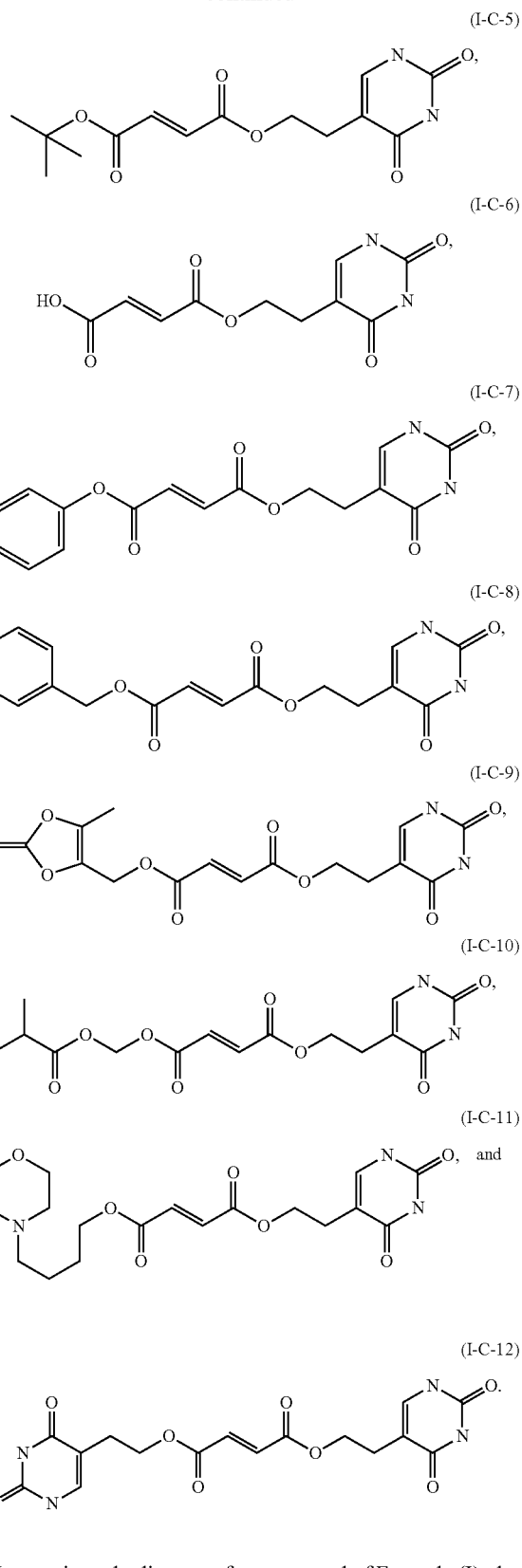

In certain embodiments of a compound of Formula (I), the compound is chosen from a compound of Formula (I-D-1) and Formula (I-D-2), or a pharmaceutically acceptable salt of any of the foregoing:

(I-D-1)

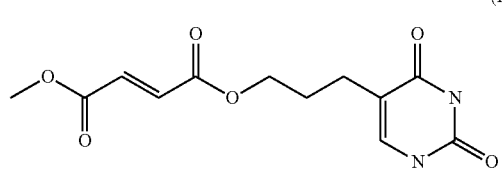

and (I-D-2)

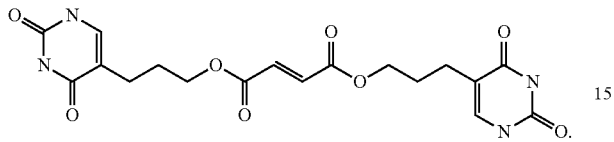

In certain embodiments of a compound of Formula (I), the compound is chosen from a compound of Formula (I-E-1) and Formula (I-E-2), or a pharmaceutically acceptable salt of any of the foregoing:

(I-E-1)

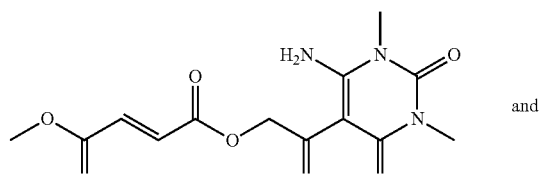

and (I-E-2)

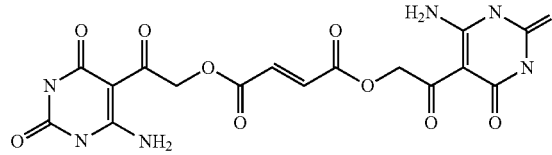

In certain embodiments of a compound of Formula (I), the compound is chosen from a compound of Formula (I-F-1), Formula (I-F-2), Formula (I-F-3), Formula (I-F-4), Formula (I-F-5), Formula (I-F-6), Formula (I-F-7), Formula (I-F-8), Formula (I-F-9), Formula (I-F-10), Formula (I-F-11), and Formula (I-F-12), or a pharmaceutically acceptable salt of any of the foregoing:

(I-F-1)

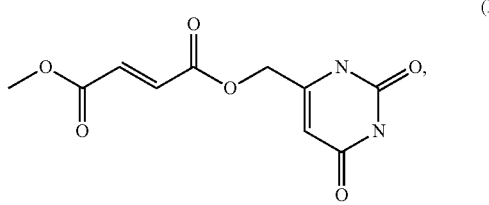

(I-F-2)

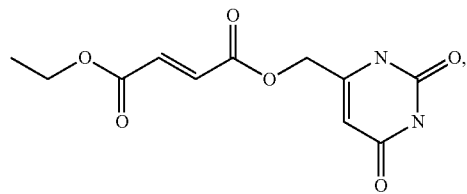

(I-F-3)

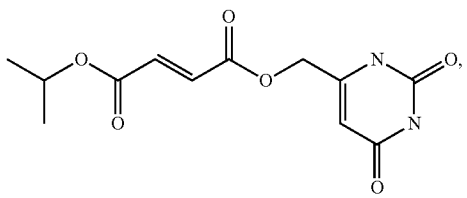

(I-F-4)

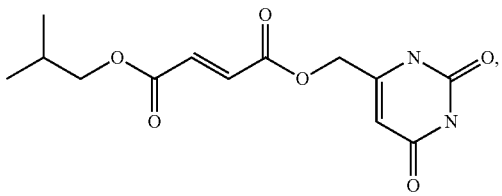

(I-F-5)

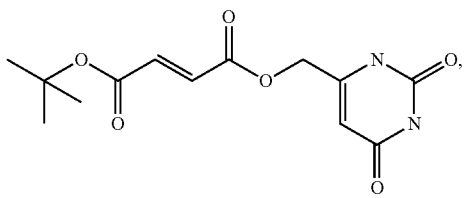

(I-F-6)

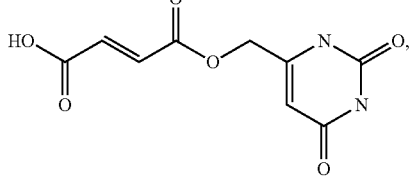

(I-F-7)

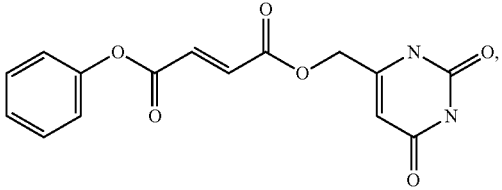

(I-F-8)

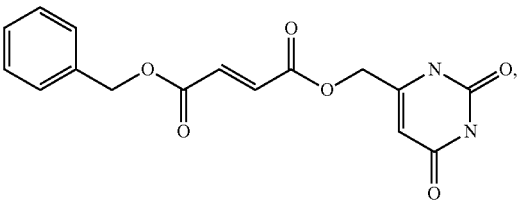

(I-F-9)

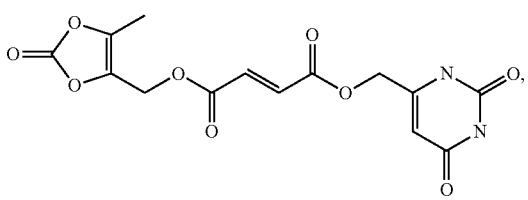

(I-F-10)
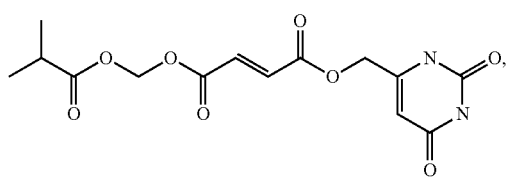

(I-F-11)
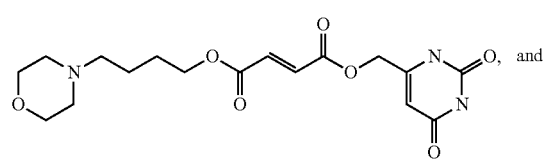

(I-F-12)
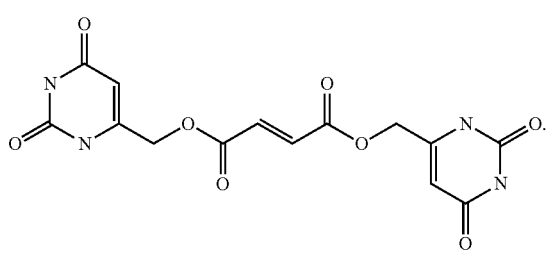

In certain embodiments of a compound of Formula (I), the compound is chosen from a compound of Formula (I-G-1) and Formula (I-G-2), or a pharmaceutically acceptable salt of any of the foregoing:

(I-G-1)
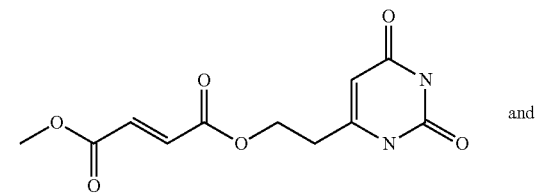

and (I-G-2)
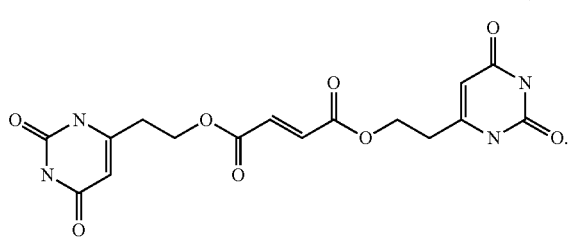

In certain embodiments of a compound of Formula (I), the compound is chosen from a compound of Formula (I-H-1) and Formula (I-H-2), or a pharmaceutically acceptable salt of any of the foregoing:

(I-H-1)
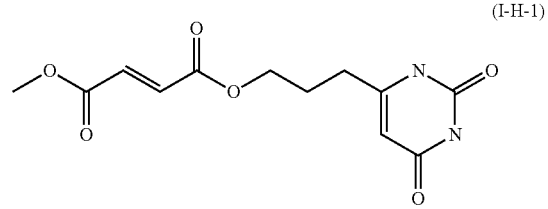

and (I-H-2)
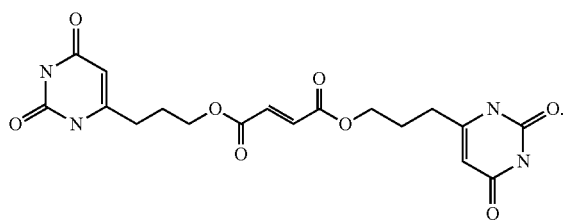

(I-B-1)
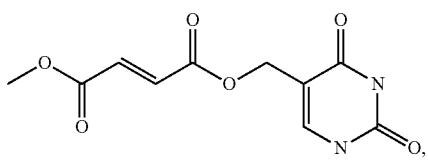

(I-B-2)
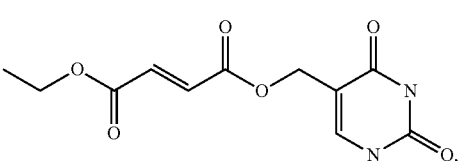

(I-B-3)
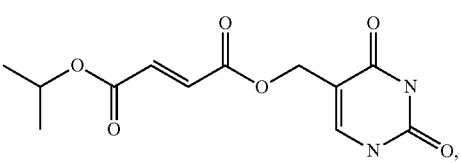

(I-B-4)
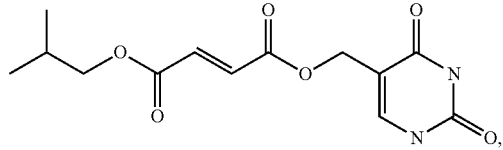

(I-B-5)
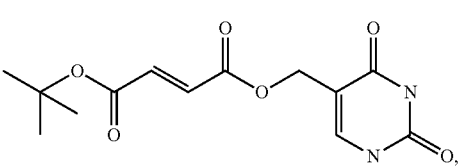

-continued (I-B-6)
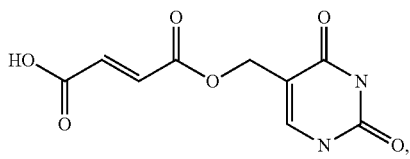

(I-B-7)
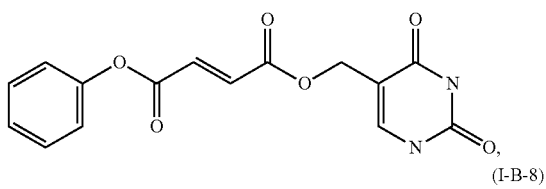

(I-B-8)

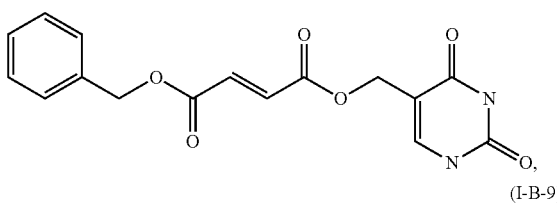

(I-B-9)

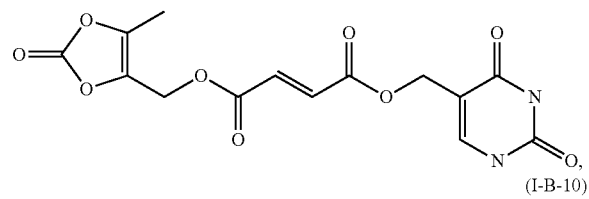

(I-B-10)

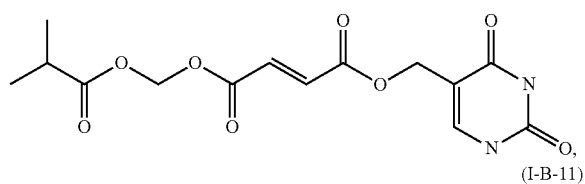

(I-B-11)

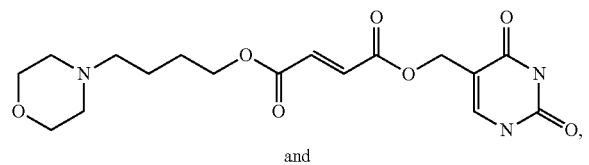

and (I-B-12)

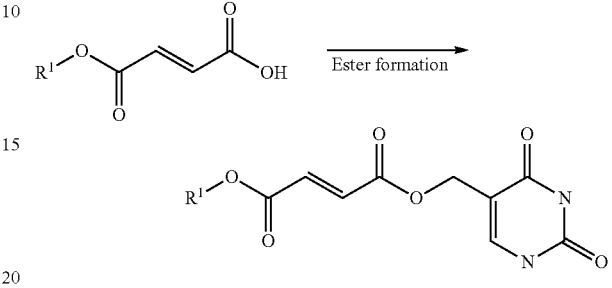

Synthesis

Compounds disclosed herein may be obtained via the synthetic method illustrated in Scheme I-A. General synthetic methods useful in the synthesis of compounds described herein are available in the art. Starting materials useful for preparing compounds and intermediates thereof and/or practicing methods described herein are commercially available or can be prepared by well-known synthetic methods. The methods presented in the schemes provided by the present disclosure are illustrative rather than comprehensive. It will be apparent to those skilled in the art that many modifications, both to materials and methods, may be practiced without departing from the scope of the disclosure.

Fumarate compounds of Formula (I) can be prepared according to Scheme I-A:

Scheme I-A wherein $R^1$ is as defined herein. In certain embodiments of Scheme I-A, $R^1$ is $C_{1-6}$ alkyl such as methyl, ethyl, propyl, isopropyl, butyl, and tert-butyl.

Pharmaceutical Compositions

Pharmaceutical compositions provided by the present disclosure may comprise a therapeutically effective amount of a compound of Formula (I) together with a suitable amount of one or more pharmaceutically acceptable vehicles so as to provide a composition for proper administration to a patient. Suitable pharmaceutical vehicles are described in the art.

In certain embodiments, a compound of Formula (I) may be incorporated into pharmaceutical compositions to be administered orally. Oral administration of such pharmaceutical compositions may result in uptake of a compound of Formula (I) throughout the intestine and entry into the systemic circulation. Such oral compositions may be prepared in a manner known in the pharmaceutical art and comprise a compound of Formula (I) and at least one pharmaceutically acceptable vehicle. Oral pharmaceutical compositions may include a therapeutically effective amount of a compound of Formula (I) and a suitable amount of a pharmaceutically acceptable vehicle, so as to provide an appropriate form for administration to a patient.

Compounds of Formula (I) may be incorporated into pharmaceutical compositions to be administered by any other appropriate route of administration including intradermal, intramuscular, intraperitoneal, intravenous, subcutaneous, intranasal, epidural, oral, sublingual, intracerebral, intravaginal, transdermal, rectal, inhalation, or topical.

Pharmaceutical compositions comprising a compound of Formula (I) and may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of compounds of Formula (I) or crystalline forms thereof and one or more pharmaceutically acceptable vehicles into formulations that can be used pharmaceutically. Proper formulation is dependent upon the route of administration chosen. Pharmaceutical compositions provided by the present disclosure may take the form of solutions, suspensions, emulsion, tablets, pills, pellets, capsules, capsules containing liquids, powders, sustained-release formulations, suppositories, emulsions, aerosols, sprays, suspensions, or any other form suitable for administration to a patient.

Pharmaceutical compositions provided by the present disclosure may be formulated in a unit dosage form. A unit dosage form refers to a physically discrete unit suitable as a unitary dose for patients undergoing treatment, with each unit containing a predetermined quantity of a compound of Formula (I) calculated to produce an intended therapeutic effect. A unit dosage form may be for a single daily dose, for administration 2 times per day, or one of multiple daily doses, e.g., 3 or more times per day. When multiple daily doses are used, a unit dosage form may be the same or different for each dose. One or more dosage forms may comprise a dose, which may be administered to a patient at a single point in time or during a time interval.

Pharmaceutical compositions comprising a compound of Formula (I) may be formulated for immediate release.

In certain embodiments, an oral dosage form provided by the present disclosure may be a controlled release dosage form. Controlled delivery technologies can improve the absorption of a drug in a particular region or regions of the gastrointestinal tract. Controlled drug delivery systems may be designed to deliver a drug in such a way that the drug level is maintained within a therapeutically effective window and effective and safe blood levels are maintained for a period as long as the system continues to deliver the drug with a particular release profile in the gastrointestinal tract. Controlled drug delivery may produce substantially constant blood levels of a drug over a period of time as compared to fluctuations observed with immediate release dosage forms. For some drugs, maintaining a constant blood and tissue concentration throughout the course of therapy is the most desirable mode of treatment. Immediate release of drugs may cause blood levels to peak above the level required to elicit a desired response, which may waste the drug and may cause or exacerbate toxic side effects. Controlled drug delivery can result in optimum therapy, and not only can reduce the frequency of dosing, but may also reduce the severity of side effects. Examples of controlled release dosage forms include dissolution controlled systems, diffusion controlled systems, ion exchange resins, osmotically controlled systems, erodable matrix systems, pH independent formulations, gastric retention systems, and the like.

An appropriate oral dosage form for a particular pharmaceutical composition provided by the present disclosure may depend, at least in part, on the gastrointestinal absorption properties of a compound of Formula (I) the stability of a compound of Formula (I) in the gastrointestinal tract, the pharmacokinetics of a compound of Formula (I) and the intended therapeutic profile. An appropriate controlled release oral dosage form may be selected for a particular compound of Formula (I). For example, gastric retention oral dosage forms may be appropriate for compounds absorbed primarily from the upper gastrointestinal tract, and sustained release oral dosage forms may be appropriate for compounds absorbed primarily from the lower gastrointestinal tract. Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect.

In certain embodiments, pharmaceutical compositions provided by the present disclosure may be practiced with dosage forms adapted to provide sustained release of a compound of Formula (I) upon oral administration. Sustained release oral dosage forms may be used to release drugs over a prolonged time period and are useful when it is desired that a drug or drug form be delivered to the lower gastrointestinal tract. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

An appropriate dose of a compound of Formula (I) or pharmaceutical composition comprising a compound of Formula (I) may be determined according to any one of several well-established protocols. For example, animal studies such as studies using mice, rats, dogs, and/or monkeys may be used to determine an appropriate dose of a pharmaceutical compound. Results from animal studies may be extrapolated to determine doses for use in other species, such as for example, humans.

Uses

Compounds of Formula (I) and pharmaceutical compositions thereof may be administered to a patient suffering from any disease including a disorder, condition, or symptom for which MHF is known or hereafter discovered to be therapeutically effective. Indications for which MHF has been prescribed, and hence for which a compound of Formula (I), or pharmaceutical compositions thereof are also expected to be effective, include psoriasis. Other indications for which compounds of Formula (I) may be therapeutically effective include multiple sclerosis, an inflammatory bowel disease, asthma, chronic obstructive pulmonary disease, and arthritis.

Methods of treating a disease in a patient provided by the present disclosure comprise administering to a patient in need of such treatment a therapeutically effective amount of an fumarate of Formula (I). Compounds of Formula (I) or pharmaceutical compositions thereof may provide therapeutic or prophylactic plasma and/or blood concentrations of MHF following administration to a patient.

Fumarates compounds of Formula (I) may be included in a pharmaceutical composition and/or dosage form adapted for oral administration, although fumarate of Formula (I) may also be administered by any other appropriate route, such as for example, by injection, infusion, inhalation, transdermal, or absorption through epithelial or mucosal membranes (e.g., oral, rectal, and/or intestinal mucosa).

Fumarate compounds of Formula (I) may be administered in an amount and using a dosing schedule as appropriate for treatment of a particular disease. Daily doses of a fumarate of Formula (I) may range from about 0.01 mg/kg to about 50 mg/kg, from about 0.1 mg/kg to about 50 mg/kg, from about 1 mg/kg to about 50 mg/kg, and in certain embodiments, from about 5 mg/kg to about 25 mg/kg. In certain embodiments, fumarates of Formula (I) may be administered at a dose over time from about 1 mg to about 5 g per day, from about 10 mg to about 4 g per day, and in certain embodiments from about 20 mg to about 2 g per day. An appropriate dose of a fumarate of Formula (I) may be determined based on several factors, including, for example, the body weight and/or condition of the patient being treated, the severity of the disease being treated, the incidence and/or severity of side effects, the manner of administration, and the judgment of the prescribing physician. Appropriate dose ranges may be determined by methods known to those skilled in the art.

Fumarates of Formula (I) may be assayed in vitro and in vivo for the desired therapeutic or prophylactic activity prior to use in humans. In vivo assays, for example using appropriate animal models, may also be used to determine whether administration of a fumarate of Formula (I) is therapeutically effective.

In certain embodiments, a therapeutically effective dose of a fumarate of Formula (I) may provide therapeutic benefit without causing substantial toxicity including adverse side effects. Toxicity of fumarates of Formula (I) and/or metabolites thereof may be determined using standard pharmaceutical procedures and may be ascertained by those skilled in the art. The dose ratio between toxic and therapeutic effect is the therapeutic index. A dose of a fumarate of Formula (I) may be within a range capable of establishing and maintaining a therapeutically effective circulating plasma and/or blood concentration of a fumarate of Formula (I) that exhibits little or no toxicity.

MHF prodrug of Formula (I) may be used to treat diseases, disorders, conditions, and symptoms of any of the foregoing for which MHF is known to provide or is later found to provide therapeutic benefit. MHF is known to be effective in treating psoriasis, multiple sclerosis, an inflammatory bowel disease, asthma, chronic obstructive pulmonary disease, and arthritis. Hence, fumarates of Formula (I) may be used to treat any of the foregoing diseases and disorders. The underlying etiology of any of the foregoing diseases being treated may have a multiplicity of origins. Further, in certain embodiments, a therapeutically effective amount of one or more compounds of Formula (I) may be administered to a patient, such as a human, as a preventative measure against various diseases or disorders. Thus, a therapeutically effective amount of one or more compounds of Formula (I) may be administered as a preventative measure to a patient having a predisposition for and/or history of immunological, autoimmune, and/or inflammatory diseases including psoriasis, asthma and chronic obstructive pulmonary diseases, cardiac insufficiency including left ventricular insufficiency, myocardial infarction and angina pectoris, mitochondrial and neurodegenerative diseases such as Parkinson's disease, Alzheimer's disease, Huntington's disease, retinopathia pigmentosa and mitochondrial encephalomyopathy, transplantation rejection, autoimmune diseases including multiple sclerosis, ischemia and reperfusion injury, AGE-induced genome damage, inflammatory bowel diseases such as Crohn's disease and ulcerative colitis; and NF-κB mediated diseases.

Psoriasis

Psoriasis is characterized by hyperkeratosis and thickening of the epidermis as well as by increased vascularity and infiltration of inflammatory cells in the dermis. Psoriasis vulgaris manifests as silvery, scaly, erythematous plaques on typically the scalp, elbows, knees, and buttocks. Guttate psoriasis occurs as tear-drop size lesions.

Fumaric acid esters are recognized for the treatment of psoriasis and dimethyl fumarate is approved for the systemic treatment of psoriasis in Germany (Mrowietz and Asadullah, Trends Mol Med 2005, 11(1), 43-48; and Mrowietz et al., Br J Dermatology 1999, 141, 424-429).

Efficacy of fumarates for treating psoriasis can be determined using animal models and in clinical trials.

Inflammatory Arthritis

Inflammatory arthritis includes diseases such as rheumatoid arthritis, juvenile rheumatoid arthritis (juvenile idiopathic arthritis), psoriatic arthritis, and ankylosing spondylitis produce joint inflammation. The pathogenesis of immune-mediated inflammatory diseases including inflammatory arthritis is believed to involve TNF and NK-κB signaling pathways (Tracey et al., Pharmacology & Therapeutics 2008, 117, 244-279). DMF has been shown to inhibit TNF and inflammatory diseases including inflammatory arthritis are believed to involve TNF and NK-κB signaling and therefore may be useful in treating inflammatory arthritis (Lowewe et al., J Immunology 2002, 168, 4781-4787).

The efficacy of fumarates for treating inflammatory arthritis can be determined using animal models and in clinical trials.

Multiple Sclerosis

Multiple sclerosis (MS) is an inflammatory autoimmune disease of the central nervous system caused by an autoimmune attack against the isolating axonal myelin sheets of the central nervous system. Demyelination leads to the breakdown of conduction and to severe disease with destruction of local axons and irreversible neuronal cell death. The symptoms of MS are highly varied with each individual patient exhibiting a particular pattern of motor, sensible, and sensory disturbances. MS is typified pathologically by multiple inflammatory foci, plaques of demyelination, gliosis, and axonal pathology within the brain and spinal cord, all of which contribute to the clinical manifestations of neurological disability (see e.g., Wingerchuk, Lab Invest 2001, 81, 263-281; and Virley, NeuroRx 2005, 2(4), 638-649). Although the causal events that precipitate MS are not fully understood, evidence implicates an autoimmune etiology together with environmental factors, as well as specific genetic predispositions. Functional impairment, disability, and handicap are expressed as paralysis, sensory and octintive disturbances spasticity, tremor, a lack of coordination, and visual impairment, which impact on the quality of life of the individual. The clinical course of MS can vary from individual to individual, but invariably the disease can be categorized in three forms: relapsing-remitting, secondary progressive, and primary progressive.

Studies support the efficacy of FAEs for treating MS and are undergoing phase II clinical testing (Schimrigk et al., Eur J Neurology 2006, 13, 604-610; and Wakkee and Thio, Current Opinion Investigational Drugs 2007, 8(11), 955-962).

Assessment of MS treatment efficacy in clinical trials can be accomplished using tools such as the Expanded Disability Status Scale and the MS Functional as well as magnetic resonance imaging lesion load, biomarkers, and self-reported quality of life. Animal models of MS shown to be useful to identify and validate potential therapeutics include experimental autoimmune/allergic encephalomyelitis (EAE) rodent models that simulate the clinical and pathological manifestations of MS and nonhuman primate EAE models.

Inflammatory Bowel Disease (Crohn's Disease, Ulcerative Colitis)

Inflammatory bowel disease (IBD) is a group of inflammatory conditions of the large intestine and in some cases, the small intestine that includes Crohn's disease and ulcerative colitis. Crohn's disease, which is characterized by areas of inflammation with areas of normal lining in between, can affect any part of the gastrointestinal tract from the mouth to the anus. The main gastrointestinal symptoms are abdominal pain, diarrhea, constipation, vomiting, weight loss, and/or weight gain. Crohn's disease can also cause skin rashes, arthritis, and inflammation of the eye. Ulcerative colitis is characterized by ulcers or open sores in the large intestine or colon. The main symptom of ulcerative colitis is typically constant diarrhea with mixed blood of gradual onset. Other types of intestinal bowel disease include collagenous colitis, lymphocytic colitis, ischaemic colitis, diversion colitis, Behcet's colitis, and indeterminate colitis.

FAEs are inhibitors of NF-κB activation and therefore may be useful in treating inflammatory diseases such as Crohn's disease and ulcerative colitis (Atreya et al., J Intern Med 2008, 263(6), 59106).

The efficacy of fumarates for treating inflammatory bowel disease can be evaluated using animal models and in clinical trials. Useful animal models of inflammatory bowel disease are known.

Asthma

Asthma is reversible airway obstruction in which the airway occasionally constricts, becomes inflamed, and is lined with an excessive amount of mucus. Symptoms of asthma include dyspnea, wheezing, chest tightness, and cough. Asthma episodes may be induced by airborne allergens, food allergies, medications, inhaled irritants, physical exercise, respiratory infection, psychological stress, hormonal changes, cold weather, or other factors.

As an inhibitor of NF-κB activation and as shown in animal studies (Joshi et al., US 2007/0027076) FAEs may be useful in treating pulmonary diseases such as asthma and chronic obstructive pulmonary disorder.

The efficacy of fumarates of Formula (I) for treating asthma can be assessed using animal models and in clinical trials.

Chronic Obstructive Pulmonary Disease

Chronic obstructive pulmonary disease (COPD), also known as chronic obstructive airway disease, is a group of diseases characterized by the pathological limitation of airflow in the airway that is not fully reversible, and includes conditions such as chronic bronchitis, emphysema, as well as other lung disorders such as asbestosis, pneumoconiosis, and pulmonary neoplasms (see, e.g., Barnes, Pharmacological Reviews 2004, 56(4), 515-548). The airflow limitation is usually progressive and associated with an abnormal inflammatory response of the lungs to noxious particles and gases. COPD is characterized by a shortness of breath the last for months or years, possibly accompanied by wheezing, and a persistent cough with sputum production. COPD is most often caused by tobacco smoking, although it can also be caused by other airborne irritants such as coal dust, asbestos, urban pollution, or solvents. COPD encompasses chronic obstructive bronchiolitis with fibrosis and obstruction of small airways, and emphysema with enlargement of airspaces and destruction of lung parenchyma, loss of lung elasticity, and closure of small airways.

The efficacy of administering at least one compound of Formula (I) for treating chronic obstructive pulmonary disease may be assessed using animal models of chronic obstructive pulmonary disease and in clinical studies. For example, murine models of chronic obstructive pulmonary disease are known.

Neurodegenerative Disorders

Neurodegenerative diseases such as Parkinson's disease, Alzheimer's disease, Huntington's disease and amyoptrophic lateral sclerosis are characterized by progressive dysfunction and neuronal death. NF-κB inhibition has been proposed as a therapeutic target for neurodegenerative diseases (Camandola and Mattson, Expert Opin Ther Targets 2007, 11(2), 123-32).

Parkinson's Disease

Parkinson's disease is a slowly progressive degenerative disorder of the nervous system characterized by tremor when muscles are at rest (resting tremor), slowness of voluntary movements, and increased muscle tone (rigidity). In Parkinson's disease, nerve cells in the basal ganglia, e.g., substantia nigra, degenerate, and thereby reduce the production of dopamine and the number of connections between nerve cells in the basal ganglia. As a result, the basal ganglia are unable to smooth muscle movements and coordinate changes in posture as normal, leading to tremor, incoordination, and slowed, reduced movement (bradykinesia) (Blandini, et al., Mol. Neurobiol. 1996, 12, 73-94).

The efficacy of compounds of Formula (I) for treating Parkinson's disease may be assessed using animal and human models of Parkinson's disease and in clinical studies.

Alzheimer's Disease

Alzheimer's disease is a progressive loss of mental function characterized by degeneration of brain tissue, including loss of nerve cells and the development of senile plaques and neurofibrillary tangles. In Alzheimer's disease, parts of the brain degenerate, destroying nerve cells and reducing the responsiveness of the maintaining neurons to neurotransmitters. Abnormalities in brain tissue consist of senile or neuritic plaques, e.g., clumps of dead nerve cells containing an abnormal, insoluble protein called amyloid, and neurofibrillary tangles, twisted strands of insoluble proteins in the nerve cell.

The efficacy of compounds of Formula (I) for treating Alzheimer's disease may be assessed using animal and human models of Alzheimer's disease and in clinical studies.

Huntington's Disease

Huntington's disease is an autosomal dominant neurodegenerative disorder in which specific cell death occurs in the neostriatum and cortex (Martin, N Engl J Med 1999, 340, 1970-80). Onset usually occurs during the fourth or fifth decade of life, with a mean survival at age of onset of 14 to 20 years. Huntington's disease is universally fatal, and there is no effective treatment. Symptoms include a characteristic movement disorder (Huntington's chorea), cognitive dysfunction, and psychiatric symptoms. The disease is caused by a mutation encoding an abnormal expansion of CAG-encoded polyglutamine repeats in the protein, huntingtin.

The efficacy of compounds of Formula (I) for treating Huntington's disease may be assessed using animal and human models of Huntington's disease and in clinical studies.

Amyotrophic Lateral Sclerosis

Amyotrophic lateral sclerosis (ALS) is a progressive neurodegenerative disorder characterized by the progressive and specific loss of motor neurons in the brain, brain stem, and spinal cord (Rowland and Schneider, N Engl J Med 2001, 344, 1688-1700). ALS begins with weakness, often in the hands and less frequently in the feet that generally progresses up an arm or leg. Over time, weakness increases and spasticity develops characterized by muscle twitching and tightening, followed by muscle spasms and possibly tremors. The average age of onset is 55 years, and the average life expectancy after the clinical onset is 4 years. The only recognized treatment for ALS is riluzole, which can extend survival by only about three months.

The efficacy compounds of Formula (I) for treating ALS may be assessed using animal and human models of ALS and in clinical studies.

Others

Other diseases and conditions for which compounds of Formula (I) can be useful in treating include rheumatica, granuloma annulare, lupus, autoimmune carditis, eczema, sarcoidosis, and autoimmune diseases including acute disseminated encephalomyelitis, Addison's disease, alopecia greata, ankylosing spondylitis, antiphospholipid antibody syndrome, autoimmune hemolytic anemia, autoimmune hepatitis, autoimmune inner ear disease, bullous pemphigoid, Behcet's disease, celiac disease, Chagas disease, chronic obstructive pulmonary disease, Crohn's disease, dermatomyositis, diabetes mellitus type I, endometriosis, Goodpasture's syndrome, Graves' disease, Guillain-Barre syndrome, Hashimoto's disease, hidradenitis suppurativea, Kawasaki disease, IgA neuropathy, idiopathic thrombocytopenic purpura, interstitial cystitis, lupus erythematosus, mixed connective tissue disease, morphea, multiple sclerosis, myasthenia gravis, narcolepsy, neuromyotonia, pemphigus vulgaris, pernicious anaemia, psoriasis, psonatic arthritis, polymyositis, primary biliary cirrhosis, rheumatoid arthritis, schizophrena, scleroderma, Sjogren's syndrome, stiff person syndrome, temporal arteritis, ulcerative colitis, vasculitis, vitiligo, and Wegener's granulomatosis.

Administration

Fumarate compounds of Formula (I) and pharmaceutical compositions thereof may be administered orally or by any other appropriate route, for example, by infusion or bolus injection, by absorption through epithelial or mucocutaneous linings (e.g., oral mucosa, rectal, and intestinal mucosa, etc.). Other suitable routes of administration include, but are not limited to, intradermal, intramuscular, intraperitoneal, intravenous, subcutaneous, intranasal, epidural, oral, sublingual, intracerebral, intravaginal, transdermal, rectal, inhalation, or topical.

Administration may be systemic or local. Various delivery systems are known, e.g., encapsulation in liposomes, microparticles, microcapsules, capsules, etc.) that may be used to administer a compound and/or pharmaceutical composition.

The amount of a fumarate of Formula (I) that will be effective in the treatment of a disease in a patient will depend, in part, on the nature of the condition and can be determined by standard clinical techniques known in the art. In addition, in vitro or in vivo assays may be employed to help identify optimal dosage ranges. A therapeutically effective amount of a fumarate of Formula (I) to be administered may also depend on, among other factors, the subject being treated, the weight of the subject, the severity of the disease, the manner of administration, and the judgment of the prescribing physician.

For systemic administration, a therapeutically effective dose may be estimated initially from in vitro assays. For example, a dose may be formulated in animal models to achieve a beneficial circulating composition concentration range. Initial doses may also be estimated from in vivo data, e.g., animal models, using techniques that are known in the art. Such information may be used to more accurately determine useful doses in humans. One having ordinary skill in the art may optimize administration to humans based on animal data.

A dose may be administered in a single dosage form or in multiple dosage forms. When multiple dosage forms are used the amount of compound contained within each dosage form may be the same or different. The amount of a fumarate of Formula (I) contained in a dose may depend on the route of administration and whether the disease in a patient is effectively treated by acute, chronic, or a combination of acute and chronic administration.

In certain embodiments an administered dose is less than a toxic dose. Toxicity of the compositions described herein may be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. In certain embodiments, a fumarate may exhibit a high therapeutic index. The data obtained from these cell culture assays and animal studies may be used in formulating a dosage range that is not toxic for use in humans. A dose of a fumarate provided by the present disclosure may be within a range of circulating concentrations in for example the blood, plasma, or central nervous system, that include the effective dose and that exhibits little or no toxicity. A dose may vary within this range depending upon the dosage form employed and the route of administration utilized. In certain embodiments, an escalating dose may be administered.

Combination Therapy

Methods provided by the present disclosure further comprise administering one or more pharmaceutically active compounds in addition to a fumarate of Formula (I). Such compounds may be provided to treat the same disease or a different disease than the disease being treated with the MHF prodrug of Formula (I).

In certain embodiments, a fumarate of Formula (I) may be used in combination with at least one other therapeutic agent. In certain embodiments, a fumarate of Formula (I) may be administered to a patient together with another compound for treating diseases and conditions involving immunological, autoimmune, and/or inflammatory processes including: psoriasis; asthma, chronic obstructive pulmonary diseases, and arthritis; cardiac insufficiency including left ventricular insufficiency, myocardial infarction and angina pectoris; mitochondrial and neurodegenerative diseases such as Parkinson's disease, Alzheimer's disease, Huntington's disease, retinopathia pigmentosa and mitochondrial encephalomyopathy; transplantation rejection; autoimmune diseases including multiple sclerosis (MS); ischemia and reperfusion injury (AGE-induced genome damage; and others. In certain embodiments, a fumarate of Formula (I) may be administered to a patient together with another compound for treating psoriasis, multiple sclerosis, an inflammatory bowel disease, asthma, chronic obstructive pulmonary disease, and arthritis.

A fumarate of Formula (I) and the at least one other therapeutic agent may act additively or, and in certain embodiments, synergistically. The at least one additional therapeutic agent may be included in the same dosage form as a fumarate of Formula (I) or may be provided in a separate dosage form. Methods provided by the present disclosure can further include, in addition to administering a fumarate of Formula (I), administering one or more therapeutic agents effective for treating the same or different disease than the disease being treated by a fumarate of Formula (I). Methods provided by the present disclosure include administration of a fumarate of Formula (I) and one or more other therapeutic agents provided that the combined administration does not inhibit the therapeutic efficacy of the MHF prodrug and/or does not typically produce significant and/or substantial adverse combination effects.

In certain embodiments, dosage forms comprising a fumarate of Formula (I) may be administered concurrently with the administration of another therapeutic agent, which may be part of the same dosage form as, or in a different dosage form than that comprising a fumarate of Formula (I). A fumarate of Formula (I) may be administered prior or subsequent to administration of another therapeutic agent. In certain embodiments of combination therapy, the combination therapy may comprise alternating between administering a fumarate of Formula (I) and a composition comprising another therapeutic agent, e.g., to minimize adverse drug effects associated with a particular drug. When a fumarate of Formula (I) is administered concurrently with another therapeutic agent that potentially may produce an adverse drug effect including, but not limited to, toxicity, the other therapeutic agent may advantageously be administered at a dose that falls below the threshold at which the adverse drug reaction is elicited.

In certain embodiments, dosage forms comprising a fumarate of Formula (I) may be administered with one or more substances to enhance, modulate and/or control release, bioavailability, therapeutic efficacy, therapeutic potency, stability, and the like of a MBF prodrug of Formula (I). For example, to enhance the therapeutic efficacy of a fumarate ligand of Formula (I), the MHF prodrug of Formula (I) may be co-administered with or a dosage form comprising a fumarate of Formula (I) may comprise one or more active agents to increase the absorption or diffusion of a fumarate of Formula (I) from the gastrointestinal tract to the systemic circulation, or to inhibit degradation of the MHF prodrug of Formula (I) in the blood of a patient. In certain embodiments, a fumarate of Formula (I) may be co-administered with an active agent having pharmacological effects that enhance the therapeutic efficacy of a fumarate of Formula (I).

In certain embodiments, a fumarate of Formula (I) or a pharmaceutical composition thereof may be administered to a patient for treating psoriasis in combination with a therapy or another therapeutic agent known or believed to be effective in treating psoriasis. Drugs useful for treating psoriasis include steroids such as flurandrenolide, fluocinonide, alclometasone, amcinonide, desonide, halcinonide, triamcinolone, clobetasol, clocortolone, mometasone, desoximetasone, and halobetasol; anti-rheumatics such as etanercept, infliximab, and adalimumab; immunosuppressive agents such as cyclosporine, alefacept, and efalizumab; psoralens such as methoxsalen; and other such as calcipotriene, methotrexate, hydrocortisone/pramoxine, acitretin, betamethasone/calcipotriene, tazaraotene, benzocaine/pyrilamine/zinc oxide, and ustekinumab.

In certain embodiments, a fumarate of Formula (I) or a pharmaceutical composition thereof may be administered to a patient for treating inflammatory arthritis such as rheumatoid arthritis, juvenile rheumatoid arthritis, psoriatic arthritis, and ankylosing spondylitis in combination with a therapy or another therapeutic agent known or believed to be effective in treating inflammatory arthritis such as rheumatoid arthritis, juvenile rheumatoid arthritis, psoriatic arthritis, and ankylosing spondylitis.

Drugs useful for treating rheumatoid arthritis include non-steroidal anti-inflammatory agents such as ibuprofen, ketoprofen, salicylate, diclofenac, nabumetone, naproxen, meloxicam, sulindac, flurbiprofen, indomethacin, tolmetin, piroxicam, fenoprofen, oxaprozin, and etodolac; antiheumatics such as entanercept, adalimumab, infliximab, hydroxychloroquine, leflunomide, azathioprine, penicillamine, methotrexate, anakinra, auranofin, rituximab, aurothioglucose, tocilizumab, and golimumab; cox-2 inhibtors such as celecoxib and vadecoxib; corticosteroids such as triamcinolone; glucocorticoids such as methylprednisolone and prednisone; and others such as sulfasalazine.

Drugs useful for treating juvenile rheumatoid arthritis include adalimumab, abatacept, and infliximab.

Drugs useful for treating psoriatic arthritis include etanercept, adalimumab, triamcinolone, cortisone, infliximab, and golimumab.

Drugs useful for treating ankylosing spondylitis include adalimumab, celecoxib, diclofenac, etanercept, golimumab, indomethacin infliximab, naptoxen, olsalazine, salicylates, sulfindac, and triamcinolone.

In certain embodiments, a fumarate of Formula (I) or a pharmaceutical composition thereof may be administered to a patient for treating psoriatic arthritis in combination with a therapy or another therapeutic agent known or believed to be effective in treating psioriatic arthritis. Drugs useful for treating psoriatic arthritis include etanercept, adalimumab, triamcinolone, cortisone, infliximab, and golimumab.

In certain embodiments, a fumarate of Formula (I) or a pharmaceutical composition thereof may be administered to a patient for treating autoimmune diseases such as lupus in combination with a therapy or another therapeutic agent known or believed to be effective in treating autoimmune diseases such as lupus. Drugs useful for treating lupus include hydroxychlooquine, triamcinolone, salicylate, azathioprine, and abetimus.

In certain embodiments, a fumarate of Formula (I) or a pharmaceutical composition thereof may be administered to a patient for treating multiple sclerosis in combination with a therapy or another therapeutic agent known or believed to be effective in treating multiple sclerosis. Drugs useful for treating multiple sclerosis include interferon β-1a, interferon β-1b, glatiramer, modafinil, azathioprine, predisolone, mycophenolate mofetil, mitoxantrone, and natalizumab. Other examples of drugs useful for treating MS include Examples of drugs useful for treating MS include corticosteroids such as methylprednisolone; IFN-β such as IFN-β1a and IFN-β1b; glatiramer acetate; monoclonal antibodies that bind to the very late antigen-4 (VLA-4) integrin such as natalizumab; immunomodulatory agents such as FTY 720 sphingosie-1 phosphate modulator and COX-2 inhibitors such as BW755c, piroxicam, and phenidone; and neuroprotective treatments including inhibitors of glutamate excitotoxicity and iNOS, free-radical scavengers, and cationic channel blockers; memantine; AMPA antagonists such as topiramate; and glycine-site NMDA antagonists.

In certain embodiments, a fumarate of Formula (I) or a pharmaceutical composition thereof may be administered to a patient for treating inflammatory bowel disease in combination with a therapy or another therapeutic agent known or believed to be effective in treating inflammatory bowel disease. Drugs useful for treating inflammatory bowel disease include cromolyn and mercaptopurine; and more particularly for treating Crohn's disease include certolizumab, budesonide, azathioprine, sulfasalazine, metronidazole, adalimumab, mercaptopurine, infliximab, mesalamine, and natalizumab; and for treating ulcerative colitis include balsalazide, infliximab, azathioprine, mesalamine, and cyclosporine.

In certain embodiments, fumarates provided by the present disclosure and pharmaceutical compositions thereof may be administered to a patient for treating asthma in combination with a therapy or another therapeutic agent known or believed to be effective in treating asthma, or in certain embodiments, a disease, disorder, or condition associated with asthma. Examples of drugs useful in treating asthma include albuterol, aminophylline, beclomethasone, bitolterol, budesonide, cromolyn, ephedrine, epinephrine, flunisolide, fluticasone, formoterol, hydrocortisone, isoproterenol, levalbuterol, methylprednisolone, prednisolone, prednisone, pirbuterol, metaproterenol, racepinephrine, omalizumab, oxytriphylline, mometusone, montelukast, nedocromil, oxtriphylline, pirbuterol, salmeterol, terbutaline, theophylline, triamcinolone, zafirlukast, and zileuton.

In certain embodiments, fumarates provided by the present disclosure and pharmaceutical compositions thereof may be administered to a patient for treating chronic obstructive pulmonary disease in combination with a therapy or another therapeutic agent known or believed to be effective in treating chronic obstructive pulmonary disease, or in certain embodiments, a disease, disorder, or condition associated with chronic obstructive pulmonary disease. Examples of drugs useful for treating chronic obstructive pulmonary disease include albuterol, arformoterol, azithromycin, bitolterol, epinephrine, fluticasone, formoterol, ipratropium, isoproterenol, levabuterol, metaproterenol, pirbuterol, racepinephrine, salmeterol, and tiotropium. Useful drugs for treating chronic obstructive pulmonary disease further include bronchodialators such as β2 agonists such as salbutamol, bambuterol, clenbuterol, fenoterol, and formoterol; M3 antimuscarinics such as ipratropium; leukotriene antagonists such as montelukast, pranlukast, and zafirlukast; cromones such as cromoglicate and nedocromil; xanthines such as theophylline; corticosteroids such as beclomethasone, mometasone, and fluticasone; and TNF antagonists such as infliximab, adalimumab, and etanercept. Other treatments for chronic obstructive pulmonary disease include oxygen therapy, and pulmonary rehabilitation.

In certain embodiments, prodrugs provided by the present disclosure and pharmaceutical compositions thereof may be administered to a patient for treating angiogenesis in combination with a therapy or another therapeutic agent known or believed to be effective in treating angiogenesis. Useful drugs for treating angiogenesis include angiostatin, endostatin, vitaxin, bevacizumab, thalidomide, batimastat, marimastat, carboxyamidotraizole, TNP-470, CM101, IFN-α, IL-12, platelet factor-4, suramin, SU5416, thrombospondin, VEGFR, angiostatic steroids, cartilage-derived angiogenesis inhibitory factor, matrix metalloproteinase inhibitors, 2-methoxyestradiol, tecogalan, thrombospondin, prolactin, αvβ3 inhibitors, and linomide.

In certain embodiments, prodrugs provided by the present disclosure and pharmaceutical compositions thereof may be administered to a patient for treating transplant rejection in combination with a therapy or another therapeutic agent known or believed to be effective in treating transplant rejection. Useful drugs for treating transplant rejection include calcineurin inhibitors such as cyclosporine and tacrolimus, mTOR inhibitors such as sirolimus and everolimus, anti-proliferatives such as azathioprine and mycophenolic acid; corticosteroids such as monoclonal anti-IL2Rα receptor antibodies including basiliximab and daclizumab; and polyclonal anti-T-cell antibodies including anti-thymocyte globulin and anti-lymphocyte globulin.

In certain embodiments, prodrugs provided by the present disclosure and pharmaceutical compositions thereof may be administered to a patient for treating transplantation rejection in combination with a therapy or another therapeutic agent known or believed to be effective in treating transplantation rejection. Examples of drugs useful in transplantation rejection include corticosteroids such as dexamethasone, prednisolone, and prednisone; globulins such as antilymphocyte globulin and antithymocyte globulin; macrolide immunosuppressants such as sirolimus, tacrolimus, and everolimus; mitotic inhibitors such as azathiprine, cylophosphamide, and methotrexate; monoclonal antibodies such as basiliximab, daclizumab, infliximab, muromonoab; fungal metabolites such as cyclosporine; and others such as glatiramer and mycophenolate.

In certain embodiments, prodrugs provided by the present disclosure and pharmaceutical compositions thereof may be administered to a patient for treating cardiac insufficiency in combination with a therapy or another therapeutic agent known or believed to be effective in treating cardiac insufficiency. Useful drugs for treating cardiac insufficiency include antitensin-modulating agents, diuretics such as furosemide, bumetanie, hydrochlorothiazide, chlorthalidone, chlorthiazide, spironolactone, eplerenone: beta blockers such as bisoprolol, carvedilol, and metroprolol; positive inotropes such as digoxin, milrinone, and dobutamine; alternative vasodilators such as isosorbide dinitrate/hydralazine; aldosterone receptor antagonists; recombinant neuroendocrine hormones such as nesiritide; and vasopressin receptor antagonists such as tolvaptan and conivaptan.

In certain embodiments, prodrugs provided by the present disclosure and pharmaceutical compositions thereof may be administered to a patient for treating a mitochondrial disease such as a neurodegenerative disorder in combination with a therapy or another therapeutic agent known or believed to be effective in treating a mitochondrial disease such as a neurodegenerative disorder. In certain embodiments, a neurodegenerative disorder is chosen from Alzheimer's disease, Parkinson's disease, Huntington's disease, and amyotrophic lateral sclerosis.

Therapeutic agents useful for treating Parkinson's disease include dopamine precursors such levodopa, dopamine agonists such as bromocriptine, pergolide, pramipexole, and ropinirole, MAO-B inhibitors such as selegiline, anticholinergic drugs such as benztropine, trihexyphenidyl, tricyclic antidepressants such as amitriptyline, amoxapine, clomipramine, desipramine, doxepin, imipramine, maprotiline, nortriptyline, protriptyline, amantadine, and trimipramine, some antihistamines such as diphenhydramine; antiviral drugs such as amantadine; and beta blockers such as propranolol.

Useful drugs for treating Alzheimer's disease include rosiglitazone, roloxifene, vitamin E, donepezil, tacrine, rivastigmine, galantamine, and memantine.

Useful drugs for treating symptoms of Huntington's disease include antipsychotics such as haloperidol, chiorpromazine and olanzapine to control hallucinations, delusions and violent outbursts; antidepressants such as fluoxetine, sertraline, and nortryiptyline to control depression and obsessive-compulsive behavior; tranquilizers such as benzodiazepines, paroxetine, venflaxin and beta-blockers to control anxiety and chorea; mood stabilizers such as lithium, valproate, and carbamzepine to control mania and bipolar disorder; and botulinum toxin to control dystonia and jaw clenching. Useful drugs for treating symptoms of Huntington's disease further include selective serotonin reuptake inhibitors (SSRI) such as fluoxetine, paroxetine, sertraline, escitalopram, citalopram, fluvosamine; norepinephrine and serotoiun reuptake inhibitors (NSRI) such as venlafaxine and duloxetine, benzodiazepines such as clonazepam, alprazolam, diazepam, and lorazepam, tricyclic antidepressants such as amitriptyline, nortnriptyline, and imipramine; and atypical antidepressants such as busipirone, bupriopion, and mirtazepine for treating the symptoms of anxiety and depression; atomoxetine, dextroamphetamine, and modafinil for treating apathy symptoms; amantadine, memantine, and tetrabenazine for treating chorea symptoms; citalopram, atomoxetine, memantine, rivastigmine, and donepezil for treating cognitive symptoms; lorazepam and trazedone for treating insomma; valproate, carbamazepine and lamotrigine for treating symptoms of irritability; SSRI antidepressants such as fluoxetine, paroxetine, sertaline, and fluvoxamine, NSRI antidepressants such as venlafaxine, and others such as mirtazepine, clomipramine, lomotrigine, gabapentin, valproate, carbamazepine, olanzapine, rispiridone, and quetiapine for treating symptoms of obsessive-compulsive disorder; haloperidol, quetiapine, clozapine, risperidone, olanzapine, ziprasidone, and aripiprazole for treating psychosis; and pramipexole, levodopa and amantadine for treating rigidity.

Useful drugs for treating ALS include riluzole. Other drugs of potential use in treating ALS include memantine, tamoxifen, thalidomide, ceftriaxone, sodium phenyl butyrate, celecoxib, glatiramer acetate, busipirone, creatine, minocycline, coenzyme Q10, oxandrolone, IGF-1, topiramate, xaliproden, and indinavir. Drugs such as baclofen and diazepam can be useful in treating spasticity associated with ALS.

In certain embodiments, a fumarate of Formula (I) or a pharmaceutical composition thereof may be administered to a patient in combination with a therapy or another therapeutic agent known or believed to be effective in inhibiting TNF function.

Examples of drugs known to inhibit TNF function include infliximab, adalimumab, etanercept, certolizumab, golimumab, pentoxifylline, quanylhydrozone, thalidomide, flavonoids such as narigenin, resveratol and quecetin, alkaloids such as lycorine, terpenes such as acanthoic acid, fatty acids such as 13-HOA, and retinoids such as retinoic acid.

EXAMPLES

The following examples describe in detail the synthesis of fumarates of Formula (I), properties of fumarates of Formula (I), and uses of fumarates of Formula (I). It will be apparent to those skilled in the art that many modifications, both to materials and methods, may be practiced without departing from the scope of the disclosure.

General Experimental Protocols

All reagents and solvents that can be purchased from commercial suppliers may be used without further purification or manipulation. Non-commercially available reagents may be synthesized from commercially available starting materials, and by adapting methods well known in the art.

Analytical LC/MS was performed on a Agilent 1100 equipped with AB Sciex API 2000 or a Waters 2790 equipped with a Waters Micromass QZ mass spectrometer and a Phenomenex Luna C-18 analytical column. Preparative HPLC purification was performed on a Agilent 1100. Both analytical and preparative HPLC used acetonitrile/water gradients containing 0.05% formic acid. Normal-phase silica gel purification was performed on a ISCO CombiFlash Companion purification system using either a mixture of methanol and dichloromethane or ethyl acetate and hexanes. Chemical names were generated with Accelrys Draw 4.1 SP1, version MDL.Draw.Editor 4.1. 100.70 (Accelrys, Inc., San Diego, Calif.).

General Synthetic Procedures

General Procedure A: Ester formation

A primary or secondary hydroxyl-containing compound (1.0 equivalent) is combined with carboxylic acid-containing compound (0.7 to 1.5 equivalents) in 1-10 mL/1.0 mmol of an inert solvent such as dichloromethane (DCM), ethyl acetate (EtOAc), N-methylpyrrolidone (NMP), N,N-dimethylformamide (DMF), N,N-dimethylacetamide (DMA, DMAc), acetonitrile (MeCN), dimethylsulfoxide (DMSO), tetrahydrofuran (THF), toluene, or mixtures thereof. To the solution, an appropriate organic secondary or tertiary base (1.0 to 3.0 equivalents) such as dicyclohexylamine (DCHA), triethylamine (TEA), or diisopropylethylamine (DIEA), a catalyst such as 4-(dimethylamino)pyridine (DMAP), and a coupling agent (0.8 to 3.0 equivalents) such as N-(3-dimethylaminopropyl)-N'-ethylcarbodiimide hydrochloride (EDAC), N,N,N',N'-tetramethyl-O-(1H-benzotriazol-1-yl)uronium hexafluorophosphate (HBTU), 1-[bis(dimethylamino)methylene]-1H-1,2,3-triazolo[4,5-b]pyridinium 3-oxid hexafluorophosphate (HATU), O-(6-chlorobenzotriazol-1-yl)-N,N,N',N'-tetramethyluronium hexafluorophosphate (HCTU), or N,N'-dicyclohexylcarbodiimide (DCC), are added. The reaction mixture is stirred from about 1 to about 24 h at a temperature between 0° C. to 40 OC. The mixture is then diluted with an appropriate organic solvent such as methyl tert-butyl ether (MTBE), diethyl ether (Et$_2$O), ethyl acetate (EtOAc), dichloromethane (DCM), or mixtures thereof, washed with water and brine, and dried over anhydrous sodium sulfate (Na$_2$SO$_4$) or magnesium sulfate (MgSO$_4$). After filtration, the organic solvents are removed under reduced pressure using a rotary evaporator. If required, the crude reaction products are further purified by well known purification techniques such as silica gel flash column chromatography, reversed-phase preparative HPLC/lyophilization, precipitation, or crystallization.

Alternatively, (2E)-3-(methoxycarbonyl)prop-2-enoic acid (methyl hydrogen fumarate, MHF), (2E)-3-(tert-butoxycarbonyl)prop-2-enoic acid (tert-butyl hydrogen fumarate), fumaric acid (FA), or a carboxylic acid-containing compound (1.0 equivalents) is added to a mixture of a halide-containing compound (0.7 to 2.5 equivalents) such as an alkyl 2-chloroacetate and an inorganic base (0.7 to 5.0 equivalents) such as an alkali carbonate, i.e., cesium bicarbonate (CsHCO$_3$), cesium carbonate (Cs$_2$CO$_3$), or potassium carbonate (K$_2$CO$_3$) in an inert solvent such as N-methylpyrrolidone (NMP), N,N-dimethylformamide (DMF), N,N-dimethylacetamide (DMA, DMAc), acetonitrile (MeCN), dimethylsulfoxide (DMSO), tetrahydrofuran (THF), toluene, or mixtures thereof. Alternatively, organic secondary and tertiary bases such as dicyclohexyl amine (DCHA), triethylamine (TEA), diisopropylethylamine (DIEA), amidine or guanidine-based bases such as 1,5-diazabicyclo[4.3.0]non-5-ene (DBN), 1,8-diazabicyclo[5.4.0]undec-7-ene (DBU), or 1,1,3,3-tetramethylguanidine (TMG); silver salts such silver(I) oxide (Ag$_2$O) or silver(I) carbonate (Ag$_2$CO$_3$); or other halide scavengers known in the art can be employed. The reaction mixture is stirred from about 1 to about 24 h at a temperature between 20° C. to 100 OC. The mixture is then diluted with an appropriate organic solvent such as methyl tert-butyl ether (MTBE), diethyl ether (Et$_2$O), ethylacetate (EtOAc), dichloromethane (DCM), or mixtures thereof, washed with water and brine, and dried over anhydrous sodium sulfate (Na$_2$SO$_4$) or magnesium sulfate (MgSO$_4$). After filtration, the organic solvents are removed under reduced pressure using a rotary evaporator. If required, the crude reaction products are further purified by well known purification techniques such as silica gel flash column chromatography, mass-guided reversed-phase preparative HPLC/lyophilization, precipitation, or crystallization.

Example 1

O4-[(2,4-Dioxo-1H-pyrimidin-5-yl)methyl]O1-methyl (E)-but-2-enedioate (4)

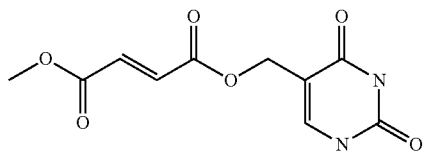 [SMILES: COC(=O)/C=C/C(=O)OCc1c[nH]c(=O)[nH]c1=O]

Following general procedure A, 5-(hydroxymethyl)-1H-pyrimidine-2,4-dione (1.5 eq) was added to a mixture of methyl hydrogen fumarate (MHF) (1.0 g, 1.0 eq), EDAC (or HBTU) (2.0 eq) and triethylamine (3.0 eq) in dichloromethane (or DMF) (20 mL). The mixture was stirred at 0° C. for 1 h and then at 20° C. overnight. The reaction was concentrated in vacuo to a residue and then purified by reverse-phase (C-18) liquid chromatography using water and acetonitrile as eluents to yield compound (1). MS (ESI): m/z 255.1 (M+H)+.

Example 2

O4-[(2,4-Dioxo-1H-pyrimidin-5-yl)methyl]O1-ethyl (E)-but-2-enedioate (2)

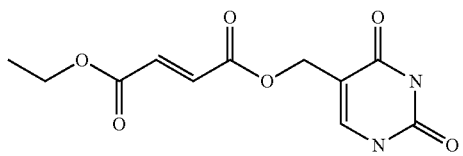 [SMILES: CCOC(=O)/C=C/C(=O)OCc1c[nH]c(=O)[nH]c1=O]

Compound (2) was prepared according to the method described in Example 1 and substituting methyl hydrogen fumarate with ethyl hydrogen fumarate. MS (ESI): m/z 269.1 (M+H)+.

Example 3

O1-[(2,4-Dioxo-1H-pyrimidin-5-yl)methyl]O4-isopropyl (E)-but-2-enedioate (3)

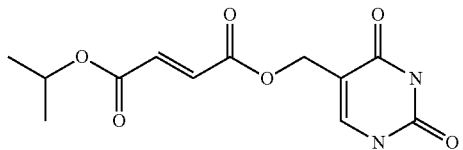 [SMILES: CC(C)OC(=O)/C=C/C(=O)OCc1c[nH]c(=O)[nH]c1=O]

Compound (3) was prepared according to the method described in Example 1 and substituting methyl hydrogen fumarate with isopropyl hydrogen fumarate. MS (ESI): m/z 283.1 (M+H)+.

Example 4

O4-tert-Butyl O1-[(2,4-dioxo-1H-pyrimidin-5-yl)methyl](E)-but-2-enedioate (4)

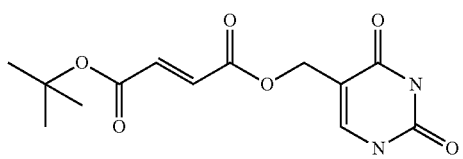 [SMILES: CC(C)(C)OC(=O)/C=C/C(=O)OCc1c[nH]c(=O)[nH]c1=O]

Compound (4) was prepared according to the method described in Example 1 and substituting methyl hydrogen fumarate with tert-butyl hydrogen fumarate. MS (ESI): m/z 297.1 (M+H)+.

Example 5

(E)-4-[(2,4-Dioxo-1H-pyrimidin-5-yl)methoxy]-4-oxo-but-2-enoic acid (5)

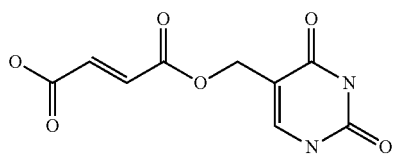 [SMILES: O=C(O)/C=C/C(=O)OCc1c[nH]c(=O)[nH]c1=O]

A solution of trifluoroacetic acid in dichloromethane (20 mL) was added to compound (4) (0.10 g). The mixture was stirred at 0° C. for 15 minutes and then at 20° C. overnight. The reaction was concentrated in vacuo to a residue and then purified by reverse-phase (C-18) liquid chromatography using water and acetonitrile as eluents to yield compound (5). MS (ESI): m/z 241.0 (M+H)+.

Example 6

Bis[(2,4-dioxo-1H-pyrimidin-5-yl)methyl](E)-but-2-enedioate (6)

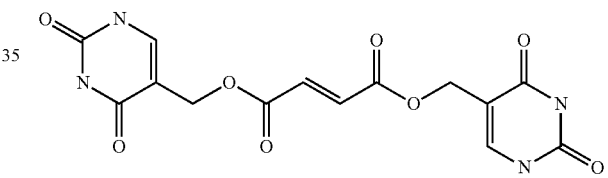

5-(Hydroxymethyl)-1H-pyrimidine-2,4-dione (3.0 eq) was added to a mixture of fumaric acid (1.0 g, 1.0 eq), EDAC (or HBTU) (4.0 eq) and triethylamine (6.0 eq) in dichloromethane (or DMF) (50 mL). The mixture was stirred at 0° C. for 1 h and then at 20° C. overnight. The reaction was concentrated in vacuo to a residue and then purified by reverse-phase (C-18) liquid chromatography using water and acetonitrile as eluents to yield compound (6). MS (ESI): m/z 365.1 (M+H)+.

Example 7

Stability of Fumarate Compounds in PBS Buffer

A mixture of a test compound (0.5 to 1.0 mg) in DMSO or DMF (0 to 0.5 mL) and Phosphate buffered saline (PBS) (0.5 to 1.0 mL, 50 mM, pH 7.4) was incubated at 25° C. for 60 min. The mixture was analyzed by a Agilent 1100 HPLC.

Compounds (1), (2), and (3) were determined to be >90% stable.

Example 8

Hydrolysis of Fumarate Compounds In Vitro

A mixture of a test compound (0.5 to 1.0 mg) in DMSO or DMF (0 to 0.5 mL) and porcine liver esterase (1.0 mg, 15 to 20 units/mg, Sigma Aldrich) in PBS buffer (0.5 to 5.0 mL, pH 7.4) was incubated at 25° C. for ca. 24 h. The mixture was diluted with methanol or acetonitrile (0.5 to 5.0 mL) and filtered through a nylon membrane (Acrodisc, 0.2 μm). The filtrate was analyzed by a Agilent 1100 HPLC.

Compounds (1), (2), and (3) were converted to MHF, monoester fumarates, and/or fumaric acid at >50%.

Description 1

Use of an Animal Model to Assess Efficacy in Treating Psoriasis

The severe, combined immunodeficient (SCID) mouse model can be used to evaluate the efficacy of compounds for treating psoriasis in humans (Boehncke, Ernst Schering Res Found Workshop 2005, 50, 213-34; and Bhagavathula et al., J Pharmacol Expt'l Therapeutics 2008, 324(3), 938-947).

SCID mice are used as tissue recipients. One biopsy for each normal or psoriatic volunteer is transplanted onto the dorsal surface of a recipient mouse. Treatment is initiated 1 to 2 weeks after transplantation. Animals with the human skin transplants are divided into treatment groups. Animals are treated twice daily for 14 days. At the end of treatment, animals are photographed and then euthanized. The transplanted human tissue along with the surrounding mouse skin is surgically removed and fixed in 10% formalin and samples obtained for microscopy. Epidermal thickness is measured. Tissue sections are stained with an antibody to the proliferation-associated antigen Ki-67 and with an anti-human CD3+ monoclonal antibody to detect human T lymphocytes in the transplanted tissue. Sections are also probed with antibodies to c-myc and β-catenin. A positive response to treatment is reflected by a reduction in the average epiderma thickness of the psoriatic skin transplants. A positive response is also associated with reduced expression of Ki-67 in keratinocytes.

Description 2

Animal Model for Assessing Therapeutic Efficacy of Fumarates for Treating Multiple Sclerosis Experiments are conducted on female mice aged 4-6 weeks belong to the C57BL/6 strain weighing 17-20 g. Experimental autoimmune encephalomyelitis (EAE) is actively induced using ≥95% pure synthetic myelin oligodendrocyte glycoprotein peptide 35-55 (MOG35-55, MEVGWYRSPFSRVVH-LYRNGK). Each mouse is anesthetized and receives 200 μg of MOG peptide and 15 μg of Saponin extract from Quilija bark emulsified in 100 μL of phosphate-buffered saline. A 25 μL volume is injected subcutaneously over four flank areas. Mice are also intraperitoneally injected with 200 ng of pertussis toxin in 200 μL of PBS. A second, identical injection of pertussis toxin is given after 48 h.

A fumarate is administered at varying doses. Control animals receive 25 μL of DMSO. Daily treatment extends from day 26 to day 36 post-immunization. Clinical scores are obtained daily from day 0 post-immunization until day 60. Clinical signs are scored using the following protocol: 0, no detectable signs; 0.5, distal tail limpness, hunched appearance and quiet demeanor; 1, completely limp tail; 1.5, limp tail and hindlimb weakness (unsteady gait and poor grip with hindlimbs); 2, unilateral partial hindlimb paralysis; 2.5, bilateral hindlimb paralysis; 3, complete bilateral hindlimb paralysis; 3.5, complete hindlimb paralysis and unilateral forelimb paralysis; 4, total paralysis of hindlimbs and forelimbs (Eugster et al., Eur J Immunol 2001, 31, 2302-2312).

Inflammation and demyelination are assessed by histology on sections from the CNS of EAE mice. Mice are sacrificed after 30 or 60 days and whole spinal cords are removed and placed in 0.32 M sucrose solution at 4° C. overnight. Tissues are prepared and sectioned. Luxol fast blue stain is used to observe areas of demyelination. Haematoxylin and eosin staining is used to highlight areas of inflammation by darkly staining the nuclei of mononuclear cells. Immune cells stained with H&E are counted in a blinded manner under a light microscope. Sections are separated into gray and white matter and each sector is counted manually before being combined to give a total for the section. T cells are immunolabeled with anti-CD3+ monoclonal antibody. After washing, sections are incubated with goat anti-rat HRP secondary antibody. Sections are then washed and counterstained with methyl green. Splenocytes isolated from mice at 30 and 60 days post-immunization are treated with lysis buffer to remove red blood cells. Cells are then resuspended in PBS and counted. Cells at a density of about 3×106 cells/mL are incubated overnight with 20 g/mL of MOG peptide. Supernatants from stimulated cells are assayed for IFN-γ protein levels using an appropriate mouse IFN-γ immunoassay system.

Description 3

Use of an Animal Model to Assess Efficacy in Treating Inflammatory Bowel Disease Animal models of inflammatory bowel disease are described by Jurjus et al., J Pharmaocol Toxicol Methods 2004, 50, 81-92; Villegas et al., Int'l Immunopharmacol 2003, 3, 1731-1741; and Murakami et al., Biochemical Pharmacol 2003, 66, 1253-1261. For example, the following protocol can be used to assess the efficacy of a compound for treating inflammatory bowel disease.

Female ICR mice are used. Mice are divided into treatment groups. Groups are given either water (control), 5% DSS in tap water is given at the beginning of the experiment to induce colitis, or various concentrations of test compound. After administering test compound for 1 week, 5% DSS in tap water is also administered to the groups receiving test compound for 1 week. At the end of the experiment, all mice are killed and the large intestine is removed. Colonic mucosa samples are obtained and homogenized. Proinflammatory mediators (e.g., IL-1α, IL-1β, TNF-α, PGE2, and PGF2α) and protein concentrations are quantified. Each excised large intestine is histologically examined and the damage to the colon scored.

Description 4

Clinical Trial for Assessing Efficacy in Treating Asthma

Adult subjects (nonsmokers) with stable mild-to-moderate asthma are enrolled (see, e.g., Van Schoor and Pauwels, Eur Respir J 2002, 19, 997-1002). A randomized, double-blind, placebo-controlled, two-period crossover design is used. On screening day 1, patients undergo a methacholine challenge (<8 mg/mL). The baseline forced expiratory volume in one second (FEV1) prior to each subsequent challenge must be within 15% of the screening baseline FEV1 obtained at the first visit. A neurokinin challenge (1×10-6 mol/mL) on screening day 2 is performed 24-72 h later. Study-period one commences within 10 days after visit two. First, a methacholine and a neurokinin-A (NKA) challenge is performed on days 1 and 0, respectively. At visit four, test compound is administered at an appropriate dose and for an appropriate period of time. On the last 2 days of the treatment period, methacholine and NKA challenges are repeated. Following treatment-period one, there is a washout period of about 5 weeks, following which the patients crossed over to another medication or placebo in study period two, which is identical to period one. Pulmonary function tests are performed using a spirometer. The metacholine challenge is performed by inhaling doubling concentrations of methacholine until the FEV1 falls by >20% of the postdiluent baseline FEV1 of that day as described by Cockcroft et al., Clin Allergy 1977, 7, 235-243. NKA challenge is performed by inhaling increasing concentrations of NKA as described by Van Schoor et al., Eur Respir J 1998, 12, 17-23. The effect of a treatment on airway responsiveness is determined using appropriate statistical methods.

Description 5

Use of an Animal Model to Assess Efficacy in Treating Chronic Obstructive Pulmonary Disease An animal model using mice chronically exposed to cigarette smoke can be used for assessing efficacy in treating emphysema (see, e.g., Martorana et al., Am J Respir Crit. Care Med 2005, 172, 848-835; and Cavarra et al., Am J Respir Crit. Care Med 2001, 164, $88_6$-890). Six-week old C57Bl/6J male mice are used. In the acute study, the mice are exposed either to room air or to the smoke of five cigarettes for 20 minutes. In the chronic study, the mice are exposed to either room air or to the smoke of three cigarettes/day for 5 days/ week for 7 months.

For the acute study, mice are divided into three groups of 40 animals each. These groups are then divided into four subgroups of 10 mice each as follows: (1) no treatment/air-exposed; (2) no treatment/smoke-exposed; (3) a first dose of test compound plus smoke-exposed; and (4) a second dose of test compound. In the first group, trolox equivalent antioxidant capacity is assessed at the end of the exposure in bronchoalveolar lavage fluid. In the second group, cytokines and chemokines are determined in bronchoalveolar lavage fluid using a commercial cytokine panel at 4 hours; and in the third group bronchoalveolar lavage fluid cell count is assessed at 24 hours.

For the chronic study, five groups of animals are used: (1) no treatment/air-exposed; (2) a first dose of a test compound plus air-exposed; (3) no treatment/smoke-exposed; (4) a second dose of the test compound plus smoke-exposed; and (5) the first dose of the test compound plus smoke exposed. Seven months after chronic exposure to room air or cigarette smoke, 5 to 12 animals from each group are killed an the lungs fixed intratracheally with formalin. Lung volume is measured by water displacement. Lungs are stained. Assessment of emphysema includes mean linear intercept and internal surface area. The volume density of macrophages, marked immunohistochemically with antimouse Mac-3 monoclonal antibodies is determined by point counting. A mouse is considered to have goblet cell metaplasia when at least one or more midsize bronchi/lung showed a positive periodic acid-Schiff staining. For the determination of desmosine, fresh lungs are homogenized, processed, and analyzed by high-pressure liquid chromatography.

Description 6

Animal Models for Assessing Therapeutic Efficacy of Fumarates for Treating Parkinson's Disease MPTP Induced Neurotoxicity MPTP, or 1-methyl-4-phenyl-1,2,3,6-tetrahydropyridine is a neurotoxin that produces a Parkinsonian syndrome in both man and experimental animals. Studies of the mechanism of MPTP neurotoxicity show that it involves the generation of a major metabolite, MPP+, formed by the activity of monoamine oxidase on MPTP. Inhibitors of monoamine oxidase block the neurotoxicity of MPTP in both mice and primates. The specificity of the neurotoxic effects of MPP+ for dopaminergic neurons appears to be due to the uptake of MPP+ by the synaptic dopamine transporter. Blockers of this transporter prevent MPP+ neurotoxicity. MPP+ has been shown to be a relatively specific inhibitor of mitochondrial complex I activity, binding to complex I at the retenone binding site and impairing oxidative phosphorylation. In vivo studies have shown that MPTP can deplete striatal ATP concentrations in mice. It has been demonstrated that MPP+ administered intrastriatally to rats produces significant depletion of ATP as well as increased lactate concentration confined to the striatum at the site of the injections. Compounds that enhance ATP production can protect against MPTP toxicity in mice.

A prodrug of Formula (I) is administered to animals such as mice or rats for three weeks before treatment with MPTP. MPTP is administered at an appropriate dose, dosing interval, and mode of administration for 1 week before sacrifice. Control groups receive either normal saline or MPTP hydrochloride alone. Following sacrifice the two striate are rapidly dissected and placed in chilled 0.1 M perchloric acid. Tissue is subsequently sonicated and aliquots analyzed for protein content using a fluorometer assay. Dopamine, 3,4-dihydroxyphenylacetic acid (DOPAC), and homovanillic acid (HVA) are also quantified. Concentrations of dopamine and metabolites are expressed as nmol/mg protein.

Prodrugs of Formula (I) that protect against DOPAC depletion induced by MPTP, HVA, and/or dopamine depletion are neuroprotective and therefore can be useful for the treatment of Parkinson's disease.

Haloperidol-Induced Hypolocomotion

The ability of a compound to reverse the behavioral depressant effects of dopamine antagonists such as haloperidol, in rodents and is considered a valid method for screening drugs with potential antiparkinsonian effects (Mandhane, et al., Eur. J. Pharmacol 1997, 328, 135-141). Hence, the ability of prodrugs of Formula (I) to block haloperidol-induced deficits in locomotor activity in mice can be used to assess both in vivo and potential anti-Parkinsonian efficacy.

Mice used in the experiments are housed in a controlled environment and allowed to acclimatize before experimental use. One and one-half (1.5) hours before testing, mice are administered 0.2 mg/kg haloperidol, a dose that reduces baseline locomotor activity by at least 50%. A test compound is administered 5-60 min prior to testing. The animals are then placed individually into clean, clear polycarbonate cages with a flat perforated lid. Horizontal locomotor activity is determined by placing the cages within a frame containing a 3×6 array of photocells interfaced to a computer to tabulate beam interrupts. Mice are left undisturbed to explore for 1 h, and the number of beam interruptions made during this period serves as an indicator of locomotor activity, which is compared with data for control animals for statistically significant differences.

6-Hydroxydopamine Animal Model

The neurochemical deficits seen in Parkinson's disease can be reproduced by local injection of the dopaminergic neurotoxin, 6-hydroxydopamine (6-OHDA) into brain regions containing either the cell bodies or axonal fibers of the nigrostriatal neurons. By unilaterally lesioning the nigrostriatal pathway on only one-side of the brain, a behavioral asymmetry in movement inhibition is observed. Although unilaterally-lesioned animals are still mobile and capable of self maintenance, the remaining dopamine-sensitive neurons on the lesioned side become supersensitive to stimulation. This is demonstrated by the observation that following systemic administration of dopamine agonists, such as apomorphine, animals show a pronounced rotation in a direction contralateral to the side of lesioning. The ability of compounds to induce contralateral rotations in 6-OHDA lesioned rats has been shown to be a sensitive model to predict drug efficacy in the treatment of Parkinson's disease.

Male Sprague-Dawley rats are housed in a controlled environment and allowed to acclimatize before experimental use. Fifteen minutes prior to surgery, animals are given an intraperitoneal injection of the noradrenergic uptake inhibitor desipramine (25 mg/kg) to prevent damage to nondopamine neurons. Animals are then placed in an anesthetic chamber and anesthetized using a mixture of oxygen and isoflurane. Once unconscious, the animals are transferred to a stereotaxic frame, where anesthesia is maintained through a mask. The top of the head is shaved and sterilized using an iodine solution. Once dry, a 2 cm long incision is made along the midline of the scalp and the skin retracted and clipped back to expose the skull. A small hole is then drilled through the skull above the injection site. In order to lesion the nigrostriatal pathway, the injection cannula is slowly lowered to position above the right medial forebrain bundle at −3.2 mm anterior posterior, −1.5 mm medial lateral from the bregma, and to a depth of 7.2 mm below the duramater. Two minutes after lowering the cannula, 6-OHDA is infused at a rate of 0.5 µL/min over 4 min, to provide a final dose of 8 µg. The cannula is left in place for an additional 5 min to facilitate diffusion before being slowly withdrawn. The skin is then sutured shut, the animal removed from the sterereotaxic frame, and returned to its housing. The rats are allowed to recover from surgery for two weeks before behavioral testing.

Rotational behavior is measured using a rotameter system having stainless steel bowls (45 cm dia×15 cm high) enclosed in a transparent Plexiglas cover around the edge of the bowl and extending to a height of 29 cm. To assess rotation, rats are placed in a cloth jacket attached to a spring tether connected to an optical rotameter positioned above the bowl, which assesses movement to the left or right either as partial (45°) or full (360°) rotations.

To reduce stress during administration of a test compound, rats are initially habituated to the apparatus for 15 min on four consecutive days. On the test day, rats are given a test compound, e.g., a prodrug of Formula (I). Immediately prior to testing, animals are given a subcutaneous injection of a subthreshold dose of apomorphine, and then placed in the harness and the number of rotations recorded for one hour. The total number of full contralatral rotations during the hour test period serves as an index of antiparkinsonian drug efficacy.

Description 7

Animal Model for Assessing Therapeutic Efficacy of Fumarates for Treating Alzheimer's Disease Heterozygous transgenic mice expressing the Swedish AD mutant gene, hAPPK670N, M671L (Tg2576; Hsiao, Learning & Memory 2001, 8, 301-308) are used as an animal model of Alzheimer's disease. Animals are housed under standard conditions with a 12:12 light/dark cycle and food and water available ad libitum. Beginning at 9 months of age, mice are divided into two groups. The first two groups of animals receive increasing doses of a fumarate, over six weeks. The remaining control group receives daily saline injections for six weeks.

Behavioral testing is performed at each drug dose using the same sequence over two weeks in all experimental groups: (1) spatial reversal learning, (2) locomotion, (3) fear conditioning, and (4) shock sensitivity.

Acquisition of the spatial learning paradigm and reversal learning are tested during the first five days of test compound administration using a water T-maze as described in Bardgett et al., Brain Res Bull 2003, 60, 131-142. Mice are habituated to the water T-maze during days 1-3, and task acquisition begins on day 4. On day 4, mice are trained to find the escape platform in one choice arm of the maze until 6 to 8 correct choices are made on consecutive trails. The reversal learning phase is then conducted on day 5. During the reversal learning phase, mice are trained to find the escape platform in the choice arm opposite from the location of the escape platform on day 4. The same performance criteria and inter-trial interval are used as during task acquisition.

Large ambulatory movements are assessed to determine that the results of the spatial reversal learning paradigm are not influenced by the capacity for ambulation. After a rest period of two days, horizontal ambulatory movements, excluding vertical and fine motor movements, are assessed in a chamber equipped with a grid of motion-sensitive detectors on day 8. The number of movements accompanied by simultaneous blocking and unblocking of a detector in the horizontal dimension are measured during a one-hour period.

The capacity of an animal for contextual and cued memory is tested using a fear conditioning paradigm beginning on day 9. Testing takes place in a chamber that contains a piece of absorbent cotton soaked in an odor-emitting solution such as mint extract placed below the grid floor. A 5-min, 3 trial 80 db, 2800 Hz tone-foot shock sequence is administered to train the animals on day 9. On day 10, memory for context is tested by returning each mouse to the chamber without exposure to the tone and foot shock, and recording the presence or absence of freezing behavior every 10 seconds for 8 minutes. Freezing is defined as no movement, such as ambulation, sniffing or stereotypy, other than respiration.

On day 11, the response of the animal to an alternate context and to the auditory cue is tested. Coconut extract is placed in a cup and the 80 dB tone is presented, but no foot shock is delivered. The presence or absence of freezing in response to the alternate context is then determined during the first 2 minutes of the trial. The tone is then presented continuously for the remaining 8 minutes of the trial, and the presence or absence of freezing in response to the tone is determined.

On day 12, the animals are tested to assess their sensitivity to the conditioning stimulus, i.e., foot shock.

Following the last day of behavioral testing, animals are anesthetized and the brains removed, post-fixed overnight, and sections cut through the hippocampus. The sections are stained to image β-amyloid plaques.

Data is analyzed using appropriate statistical methods.

Description 8

Animal Model for Assessing Therapeutic Efficacy of Fumarates for Treating Huntington's Disease Neuroprotective Effects in a Transgenic Mouse Model of Huntington's Disease Transgenic HD mice of the N171-82Q strain and non-transgenic littermates are treated with a prodrug of Formula (I) or a vehicle from 10 weeks of age. The mice are placed on a rotating rod ("rotarod"). The length of time at which a mouse falls from the rotarod is recorded as a measure of motor coordination. The total distance traveled by a mouse is also recorded as a measure of overall locomotion. Mice administered prodrugs of Formula (I) that are neuroprotective in the N171-82Q transgenic HD mouse model remain on the rotarod for a longer period of time and travel farther than mice administered vehicle.

Malonate Model of Huntington's Disease

A series of reversible and irreversible inhibitors of enzymes involved in energy generating pathways has been used to generate animal models for neurodegenerative diseases such as Parkinson's and Huntington's diseases. In particular, inhibitors of succinate dehydrogenase, an enzyme that impacts cellular energy homeostasis, has been used to generate a model for Huntington's disease.

To evaluate the effect of fumarates of Formula (I) in this malonate model for Huntington's disease, a prodrug of Formula (I) is administered at an appropriate dose, dosing interval, and route, to male Sprague-Dawley rats. A prodrug is administered for two weeks prior to the administration of malonate and then for an additional week prior to sacrifice. Malonate is dissolved in distilled deionized water and the pH adjusted to 7.4 with 0.1 M HCl. Intrastriatal injections of 1.5 µL of 3 µmol malonate are made into the left striatum at the level of the Bregma 2.4 mm lateral to the midline and 4.5 mm ventral to the dura. Animals are sacrificed at 7 days by decapitation and the brains quickly removed and placed in ice cold 0.9% saline solution. Brains are sectioned at 2 mm intervals in a brain mold. Slices are then placed posterior side down in 2% 2,3,5-tiphenyltetrazolium chloride. Slices are stained in the dark at room temperature for 30 min and then removed and placed in 4% paraformaldehyde pH 7.3. Lesions, noted by pale staining, are evaluated on the posterior surface of each section. The measurements are validated by comparison with measurements obtained on adjacent Nissl stain sections. Compounds exhibiting a neuroprotective effect and therefore potentially useful in treating Huntington's disease show a reduction in malonate-induced lesions.

Description 9

Animal Model for Assessing Therapeutic Efficacy of Fumarates for Treating Amyotrophic Lateral Sclerosis A murine model of SOD1 mutation-associated ALS has been developed in which mice express the human superoxide dismutase (SOD) mutation glycine-alanine at residue 93 (SOD1). These SOD1 mice exhibit a dominant gain of the adverse property of SOD, and develop motor neuron degeneration and dysfunction similar to that of human ALS. The SOD1 transgenic mice show signs of posterior limb weakness at about 3 months of age and die at 4 months. Features common to human ALS include astrocytosis, microgliosis, oxidative stress, increased levels of cyclooxygenase/prostaglandin, and, as the disease progresses, profound motor neuron loss.

Studies are performed on transgenic mice overexpressing human Cu/Zn-SOD G93A mutations (B6SJL-TgN (SOD1-G93A) 1 Gur) and non-transgenic B6/SJL mice and their wild litter mates. Mice are housed on a 12-hr day/light cycle and (beginning at 45 d of age) allowed ad libitum access to either test compound-supplemented chow, or, as a control, regular formula cold press chow processed into identical pellets. Genotyping can be conducted at 21 days of age as described in Gurney et al., Science 1994, 264(5166), 1772-1775. The SOD1 mice are separated into groups and treated with a test compound, e.g., an MHF prodrug, or serve as controls.

The mice are observed daily and weighed weekly. To assess health status mice are weighed weekly and examined for changes in lacrimation/salivation, palpebral closure, ear twitch and pupillary responses, whisker orienting, postural and righting reflexes and overall body condition score. A general pathological examination is conducted at the time of sacrifice.

Motor coordination performance of the animals can be assessed by one or more methods known to those skilled in the art. For example, motor coordination can be assessed using a neurological scoring method. In neurological scoring, the neurological score of each limb is monitored and recorded according to a defined 4-point scale: 0—normal reflex on the hind limbs (animal will splay its hind limbs when lifted by its tail); 1—abnormal reflex of hind limbs (lack of splaying of hind limbs weight animal is lifted by the tail); 2—abnormal reflex of limbs and evidence of paralysis; 3—lack of reflex and complete paralysis; and 4—inability to right when placed on the side in 30 seconds or found dead. The primary end point is survival with secondary end points of neurological score and body weight. Neurological score observations and body weight are made and recorded five days per week. Data analysis is performed using appropriate statistical methods.

The rotarod test evaluates the ability of an animal to stay on a rotating dowel allowing evaluation of motor coordination and proprioceptive sensitivity. The apparatus is a 3 cm diameter automated rod turning at, for example, 12 rounds per min. The rotarod test measures how long the mouse can maintain itself on the rod without falling. The test can be stopped after an arbitrary limit of 120 sec. Should the animal fall down before 120 sec, the performance is recorded and two additional trials are performed. The mean time of 3 trials is calculated. A motor deficit is indicated by a decrease of walking time.

In the grid test, mice are placed on a grid (length: 37 cm, width: 10.5 cm, mesh size: 1×1 cm 2) situated above a plane support. The number of times the mice put their paws through the grid is counted and serves as a measure for motor coordination.

The hanging test evaluates the ability of an animal to hang on a wire. The apparatus is a wire stretched horizontally 40 cm above a table. The animal is attached to the wire by its forepaws. The time needed by the animal to catch the string with its hind paws is recorded (60 sec max) during three consecutive trials.

Electrophysiological measurements (EMG) can also be used to assess motor activity condition. Electromyographic recordings are performed using an electromyography apparatus. During EMG monitoring mice are anesthetized. The measured parameters are the amplitude and the latency of the compound muscle action potential (CMAP). CMAP is measured in gastrocnemius muscle after stimulation of the sciatic nerve. A reference electrode is inserted near the Achilles tendon and an active needle placed at the base of the tail. A ground needle is inserted on the lower back of the mice. The sciatic nerve is stimulated with a single 0.2 msec pulse at supramaximal intensity (12.9 mA). The amplitude (mV) and the latency of the response (ms) are measured. The amplitude is indicative of the number of active motor units, while distal latency reflects motor nerve conduction velocity.

The efficacy of test compounds can also be evaluated using biomarker analysis. To assess the regulation of protein biomarkers in SOD1 mice during the onset of motor impairment, samples of lumbar spinal cord (protein extracts) are applied to

The invention claimed is:

1. A compound according to Formula (I):

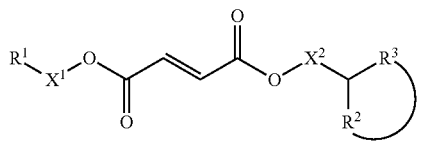

or a pharmaceutically acceptable salt thereof, wherein:
$R^1$ is selected from the group consisting of hydrogen, $C_{1-6}$ alkyl, substituted $C_{1-6}$ alkyl, $C_{1-6}$ heteroalkyl, substituted $C_{1-6}$ heteroalkyl, $C_{3-12}$ cycloalkyl, substituted $C_{3-12}$ cycloalkyl, $C_{3-12}$ heterocycloalkyl, substituted $C_{3-12}$ heterocycloalkyl, $C_{5-10}$ aryl, substituted $C_{5-10}$ aryl, $C_{5-10}$ heteroaryl, and substituted $C_{5-10}$ heteroaryl;
$R^2$ and $R^3$ together with the carbon to which they are bonded form a (2,4-dioxo-1H-pyrimidin-5-yl) ring; and
$X^1$ and $X^2$ are independently selected from the group consisting of a bond and $C_{1-6}$ alkane-diyl;
wherein each substituent group is independently selected from the group consisting of halogen, —OH, —CN, —CF$_3$, =O, —NO$_2$, benzyl, —C(O)N(R$^{21}$)$_2$, —R$^{21}$, —OR$^{21}$, —C(O)R$^{21}$, —C(O)OR$^{21}$, —N(R$^{21}$)$_2$, —NR$^{21}$C(O)R$^{21}$, and —O(O)R$^{21}$, wherein each R$^{21}$ is independently selected from the group consisting of hydrogen, $C_{1-6}$ alkyl, $C_{1-6}$ heteroalkyl, $C_{3-12}$ cycloalkyl, $C_{5-10}$ aryl, $C_{5-10}$ heteroaryl, and amino acid side chain.

2. The compound according to claim 1, wherein $R^1$ is selected from the group consisting of hydrogen, methyl, ethyl, n-propyl, isopropyl, n-butyl, tert-butyl, phenyl, benzyl, (1,3-dioxoisoindolin-2-yl), (2,5-dioxopyrrolidin-1-yl), (2,5-dioxopyrrol-1-yl), indol-1-yl, morpholin-4-yl, 1,3-oxazinan-3-yl, oxazolidin-3-yl, (1-oxoisoindolin-2-yl), (2-oxomorpholin-4-yl), (4-oxo-1-piperidyl), (2-oxopyrrolidin-1-yl), (3-oxopyrrolidin-1-yl), 1-piperidyl, tetrazol-1-yl, triazol-1-yl, 1,2,4-triazol-4-yl, 1-benzoyloxyethyl, benzoyloxymethyl, (1,3-dimethyl-2,5-dioxo-imidazolidin-4-yl), (1,3-dimethyl-2-oxo-imidazolidin-4-yl), (2,5-dioxoimidazolidin-4-yl), (2,5-dioxopyrrolidin-3-yl), (1-methyl-2,5-dioxo-imidazolidin-4-yl), (3-methyl-2,5-dioxo-imidazolidin-4-yl), (1-methyl-2,5-dioxo-pyrrolidin-3-yl), (5-methyl-2-oxo-1,3-dioxol-4-yl)methyl, (3-methyl-2-oxo-oxazolidin-4-yl), (3-methyl-2-oxo-oxazolidin-5-yl), (1-methyl-2-oxo-pyrrolidin-3-yl), (1-methyl-5-oxopyrrolidin-2-yl), (1-methyl-5-oxo-pyrrolidin-3-yl), 1-(2-methylpropanoyloxy)ethyl, 2-methylpropanoyloxymethyl, (2-oxoimidazolidin-4-yl), (2-oxooxazolidin-4-yl), (2-oxooxazolidin-5-yl), (2-oxopyrrolidin-3-yl), (5-oxopyrrolidin-2-yl), (5-oxopyrrolidin-3-yl), (2,4-dioxo-1Hpyrimidin-5-yl), and (2,4-dioxo-1H-pyrimidin-5-yl)methyl.

3. The compound according to claim 1, wherein $R^1$ is selected from the group consisting of hydrogen, methyl, ethyl, n-propyl, isopropyl, n-butyl, tert-butyl, phenyl, benzyl, (5-methyl-2-oxo-1,3-dioxol-4-yl)methyl, 1-(2-methylpropanoyloxy)ethyl, 2-methylpropanoyloxymethyl, (2,4-dioxo-1 Hpyrimidin-5-yl), and (2,4-dioxo-1H-pyrimidin-5-yl)methyl.

4. The compound according to claim 1, wherein $X^1$ and $X^2$ are independently selected from the group consisting of a bond, methane-diyl, ethane-1,1-diyl, ethane-1,2-diyl, propane-1,2-diyl, propane-1,3-diyl, 2-methylpropane-1,2-diyl, 2,2-dimethylpropane-1,3-diyl, butane-1,2-diyl, butane-1,3-diyl, butane-1,4-diyl, butane-2,3-diyl, 2,3-dimethylbutane-2,3-diyl, pentane-1,5-diyl, and hexane-1,6-diyl.

5. The compound according to claim 1, wherein $X^1$ is selected from the group consisting of a bond, methane-diyl, ethane-1,2-diyl, propane-1,3-diyl, and butane-1,4-diyl.

6. The compound according to claim 1, wherein $X^2$ is selected from the group consisting of a bond and methanediyl.

7. The compound according to claim 1, wherein $R^1$ is selected from the group consisting of hydrogen, methyl, ethyl, isopropyl, phenyl, benzyl, and (2,4-dioxo-1H-pyrimidin-5-yl); $R^2$ and $R^3$ together with the carbon to which they are bonded form a (2,4-dioxo-1H-pyrimidin-5-yl) ring; and $X^1$ and $X^2$ are independently selected from the group consisting of a bond, methane-diyl, ethane-1,2-diyl, and propane-1,3-diyl.

8. The compound according to claim 1, wherein $R^1$ is selected from the group consisting of hydrogen, methyl, ethyl, and isopropyl; $R^2$ and $R^3$ together with the carbon to which they are bonded form a (2,4-dioxo-1H-pyrimidin-5-yl) ring; $X^1$ is a bond; and $X^2$ is selected from the group consisting of a bond, methane-diyl, ethane-1,2-diyl, and propane-1,3-diyl.

9. The compound according to claim 1, wherein $R^1$ is methyl; $R^2$ and $R^3$ together with the carbon to which they are bonded form a (2,4-dioxo-1H-pyrimidin-5-yl) ring; $X^1$ is a bond; and $X^2$ is a bond.

10. The compound according to claim 1, wherein $R^1$ is methyl; $R^2$ and $R^3$ together with the carbon to which they are bonded form a (2,4-dioxo-1H-pyrimidin-5-yl) ring; $X^1$ is a bond; and $X^2$ is methane-diyl.

11. The compound according to claim 1, wherein the compound is selected from the group consisting of the compound of Formula (I-B-1), Formula (I-B-2), Formula (I-B-3), Formula (I-B-5), Formula (IB-6), and Formula (I-B-12):

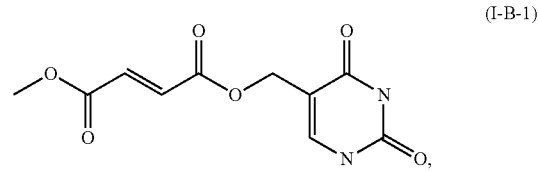

(I-B-1)

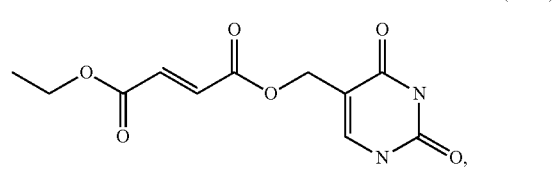

(I-B-2)

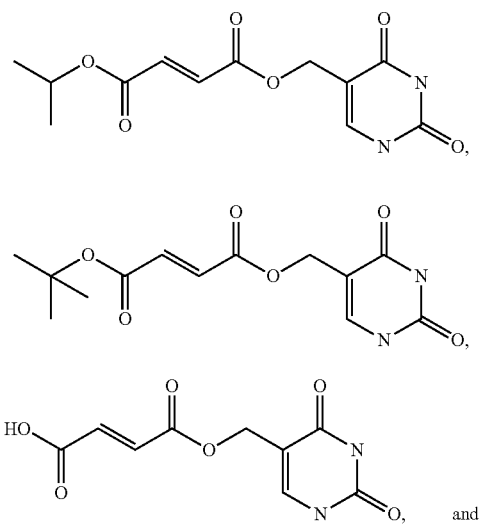
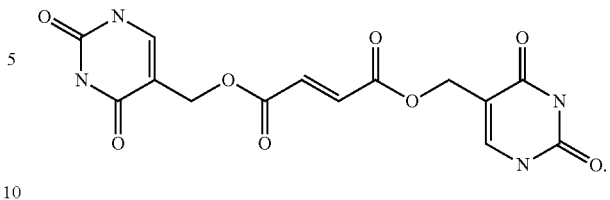
12. A pharmaceutical composition comprising a pharmaceutically acceptable vehicle and a therapeutically effective amount of a compound selected from the compounds listed in claim 11.
13. The pharmaceutical composition according to claim 12, wherein the composition is suitable for oral administration.
* * * * *